US012577346B2

(12) United States Patent
Okamura et al.

(10) Patent No.: US 12,577,346 B2
(45) Date of Patent: Mar. 17, 2026

(54) BENZOXAZINE COMPOUND-CONTAINING COMPOSITION, CURABLE RESIN COMPOSITION, AND CURED PRODUCT THEREOF

(71) Applicant: HONSHU CHEMICAL INDUSTRY CO., LTD., Tokyo (JP)

(72) Inventors: Daichi Okamura, Wakayama (JP); Takahiro Asaeda, Wakayama (JP)

(73) Assignee: HONSHU CHEMICAL INDUSTRY CO., LTD., Tokyo (JP)

( * ) Notice: Subject to any disclaimer, the term of this patent is extended or adjusted under 35 U.S.C. 154(b) by 317 days.

(21) Appl. No.: 18/032,541

(22) PCT Filed: Nov. 1, 2021

(86) PCT No.: PCT/JP2021/040192
§ 371 (c)(1),
(2) Date: Apr. 18, 2023

(87) PCT Pub. No.: WO2022/097598
PCT Pub. Date: May 12, 2022

(65) Prior Publication Data
US 2024/0002583 A1     Jan. 4, 2024

(30) Foreign Application Priority Data

Nov. 4, 2020   (JP) ................................. 2020-184536

(51) Int. Cl.
*C08G 59/50* (2006.01)
*C07D 265/16* (2006.01)
*C08G 59/06* (2006.01)
(52) U.S. Cl.
CPC ....... *C08G 59/5046* (2013.01); *C07D 265/16* (2013.01); *C08G 59/06* (2013.01)
(58) Field of Classification Search
None
See application file for complete search history.

(56) References Cited

U.S. PATENT DOCUMENTS 6,207,786 B1 * 3/2001 Ishida ..................... C08L 61/06
                                                                528/94
2019/0270907 A1    9/2019 Nakao

FOREIGN PATENT DOCUMENTS

JP    2007002064 A    1/2007
JP    2009175684 A    8/2009
JP    2011231196 A    11/2011
JP    2015025120 A    2/2015
JP    2018016684 A    2/2018
JP    2018184533 A    11/2018

OTHER PUBLICATIONS

International Preliminary Report on Patentability, dated May 8, 2023, for corresponding international application PCT/JP2021/040192 (1 page).
Notification Concerning Transmittal of International Preliminary Report on Patentability, mailed May 19, 2023, for corresponding international application PCT/JP2021/040192 (1 page).
Notification of Transmittal of Translation of the International Preliminary Report on Patentability, mailed May 19, 2023, for corresponding international application PCT/JP2021/040192 (1 page).
Written Opinion of the International Searching Authority, mailed Jan. 11, 2022, for corresponding international application PCT/JP2021/040192 (3 pages).
International Search Report (ISR) mailed Jan. 11, 2022, issued for International application No. PCT/JP2021/040192. (2 pages).

* cited by examiner

*Primary Examiner* — Megan McCulley
(74) *Attorney, Agent, or Firm* — Law Office of Katsuhiro Arai

(57) ABSTRACT

A benzoxazine compound-containing composition with a low melt viscosity, a curable resin composition, and a cured product thereof are provided. The benzoxazine compound-containing composition contains a benzoxazine compound represented by general formula (1)

and a compound group (A) having a molecular weight in the range of 1,000 to 10,000. In a gel permeation chromatography measurement using a differential refractometer as a detector, a peak area of the compound group (A) is in the range of 0.1 area % to 15 area % relative to a peak area of all components detected, and the benzoxazine compound-containing composition has a melt viscosity at 100° C. in the range of 0.1 Pa·S to 4.5 Pa·S.

5 Claims, 9 Drawing Sheets

FIG. 1

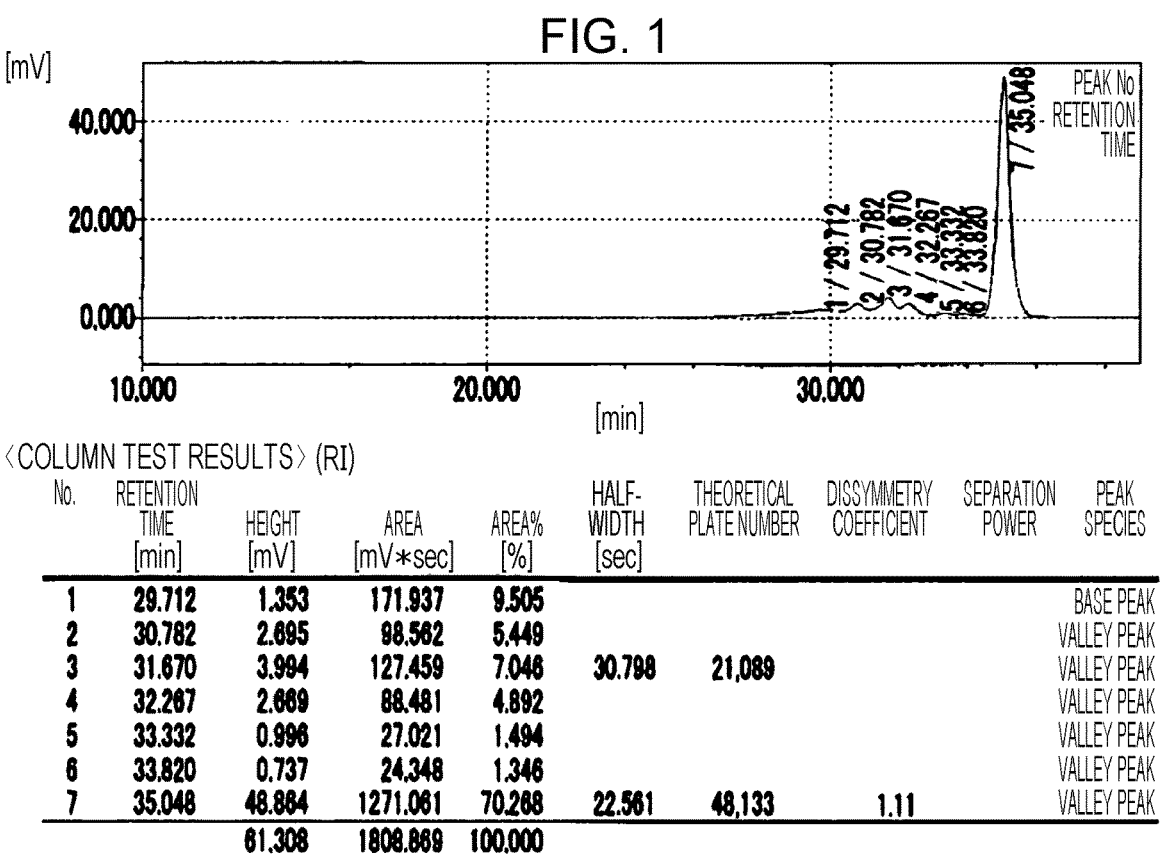

‹COLUMN TEST RESULTS› (RI)

| No. | RETENTION TIME [min] | HEIGHT [mV] | AREA [mV∗sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 29.712 | 1.353 | 171.937 | 9.505 | | | | | BASE PEAK |
| 2 | 30.782 | 2.695 | 98.562 | 5.449 | | | | | VALLEY PEAK |
| 3 | 31.670 | 3.994 | 127.459 | 7.046 | 30.798 | 21,089 | | | VALLEY PEAK |
| 4 | 32.267 | 2.669 | 88.481 | 4.892 | | | | | VALLEY PEAK |
| 5 | 33.332 | 0.996 | 27.021 | 1.494 | | | | | VALLEY PEAK |
| 6 | 33.820 | 0.737 | 24.348 | 1.346 | | | | | VALLEY PEAK |
| 7 | 35.048 | 48.884 | 1271.061 | 70.268 | 22.561 | 48,133 | 1.11 | | VALLEY PEAK |
| | | 61.308 | 1808.869 | 100.000 | | | | | |

FIG. 2

‹COLUMN TEST RESULTS› (RI)

| No. | RETENTION TIME [min] | HEIGHT [mV] | AREA [mV∗sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 30.070 | 1.038 | 146.059 | 11.256 | | | | | BASE PEAK |
| 2 | 30.832 | 1.773 | 62.315 | 4.802 | | | | | VALLEY PEAK |
| 3 | 31.710 | 3.209 | 103.944 | 8.011 | 28.446 | 24,783 | | | VALLEY PEAK |
| 4 | 32.270 | 1.461 | 40.351 | 3.110 | | | | | VALLEY PEAK |
| 5 | 33.353 | 1.446 | 40.576 | 3.127 | 24.918 | 35,733 | | | VALLEY PEAK |
| 6 | 33.878 | 0.363 | 9.461 | 0.729 | | | | | VALLEY PEAK |
| 7 | 35.087 | 33.833 | 894.890 | 68.965 | 22.752 | 47,431 | 1.17 | | VALLEY PEAK |
| | | 43.122 | 1297.597 | 100.000 | | | | | |

FIG. 3

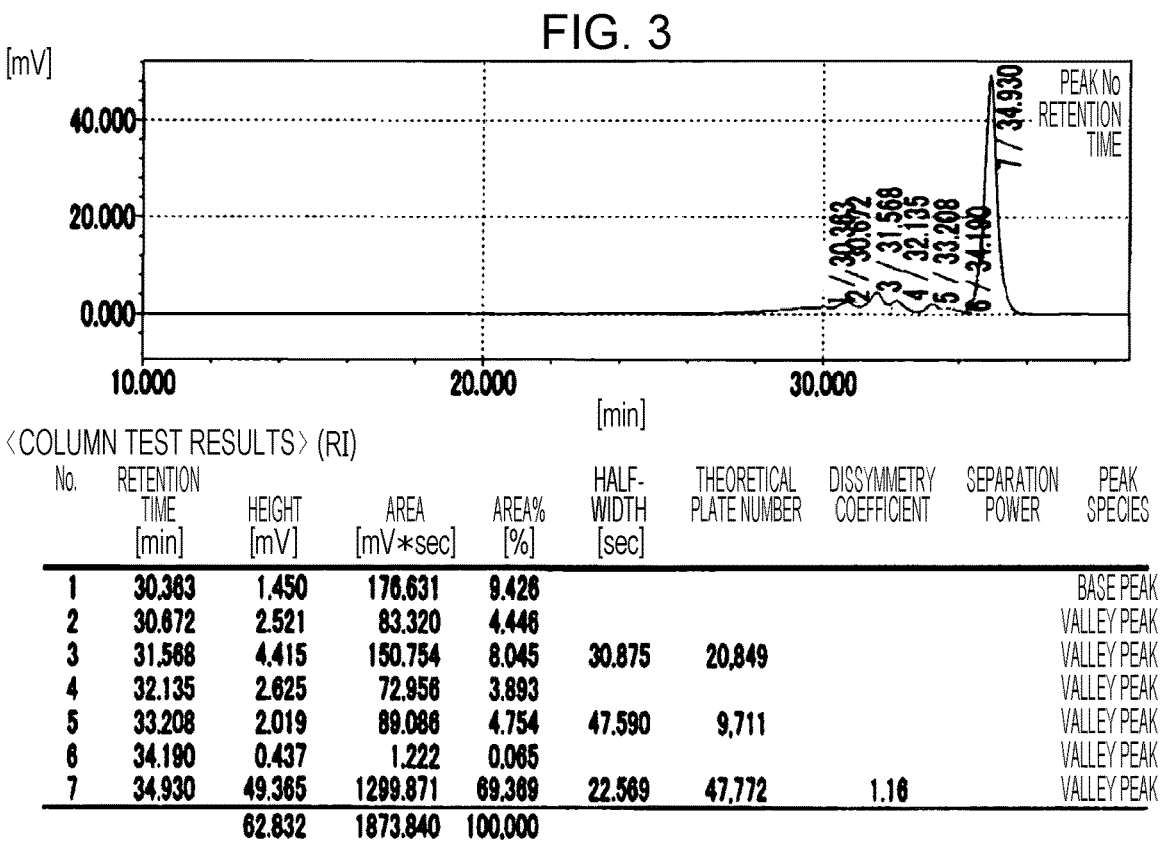

〈COLUMN TEST RESULTS〉 (RI)

| No. | RETENTION TIME [min] | HEIGHT [mV] | AREA [mV*sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 30.383 | 1.450 | 176.631 | 9.426 | | | | | BASE PEAK |
| 2 | 30.672 | 2.521 | 83.320 | 4.446 | | | | | VALLEY PEAK |
| 3 | 31.568 | 4.415 | 150.754 | 8.045 | 30.875 | 20,849 | | | VALLEY PEAK |
| 4 | 32.135 | 2.625 | 72.956 | 3.893 | | | | | VALLEY PEAK |
| 5 | 33.208 | 2.019 | 89.086 | 4.754 | 47.590 | 9,711 | | | VALLEY PEAK |
| 6 | 34.190 | 0.437 | 1.222 | 0.065 | | | | | VALLEY PEAK |
| 7 | 34.930 | 49.365 | 1299.871 | 69.369 | 22.569 | 47,772 | 1.16 | | VALLEY PEAK |
| | | 62.832 | 1873.840 | 100.000 | | | | | |

FIG. 4

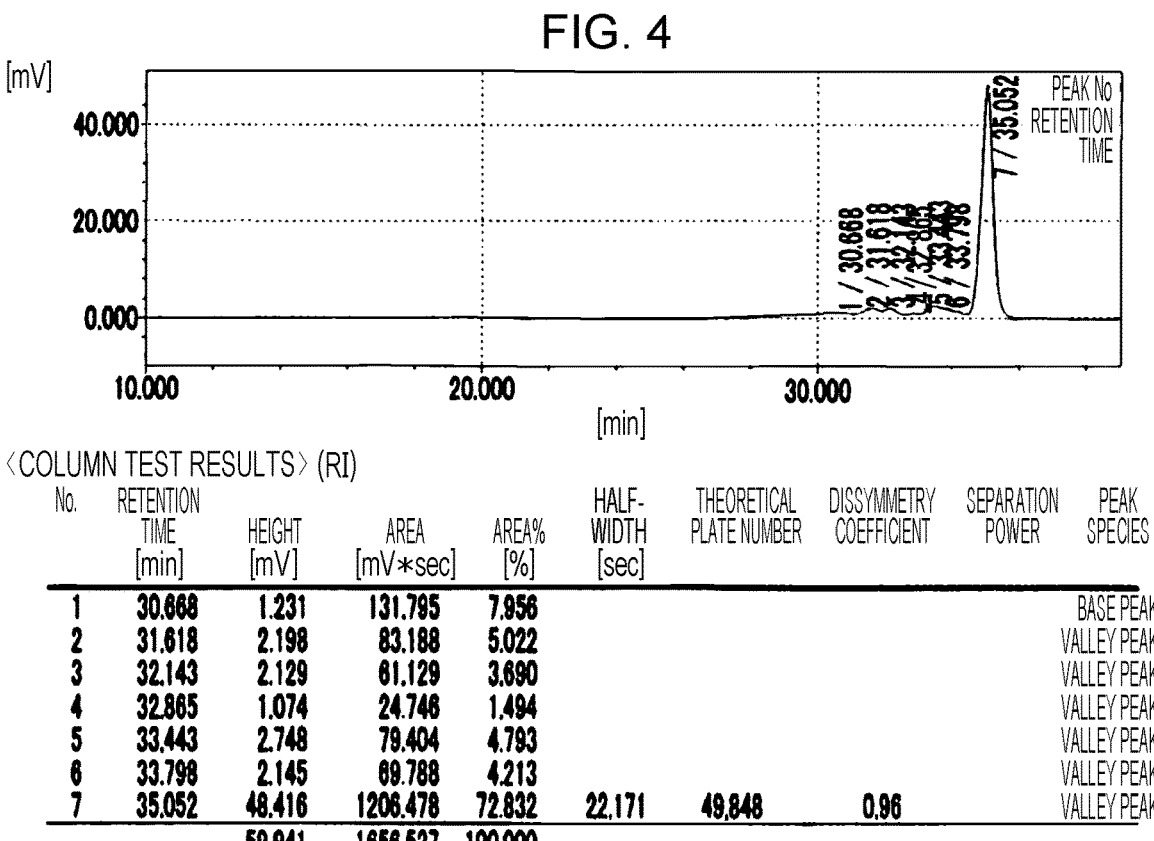

〈COLUMN TEST RESULTS〉 (RI)

| No. | RETENTION TIME [min] | HEIGHT [mV] | AREA [mV*sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 30.668 | 1.231 | 131.795 | 7.956 | | | | | BASE PEAK |
| 2 | 31.618 | 2.198 | 83.188 | 5.022 | | | | | VALLEY PEAK |
| 3 | 32.143 | 2.129 | 61.129 | 3.690 | | | | | VALLEY PEAK |
| 4 | 32.865 | 1.074 | 24.746 | 1.494 | | | | | VALLEY PEAK |
| 5 | 33.443 | 2.748 | 79.404 | 4.793 | | | | | VALLEY PEAK |
| 6 | 33.798 | 2.145 | 69.788 | 4.213 | | | | | VALLEY PEAK |
| 7 | 35.052 | 48.416 | 1206.478 | 72.832 | 22.171 | 49,848 | 0.96 | | VALLEY PEAK |
| | | 59.941 | 1656.527 | 100.000 | | | | | |

FIG. 5

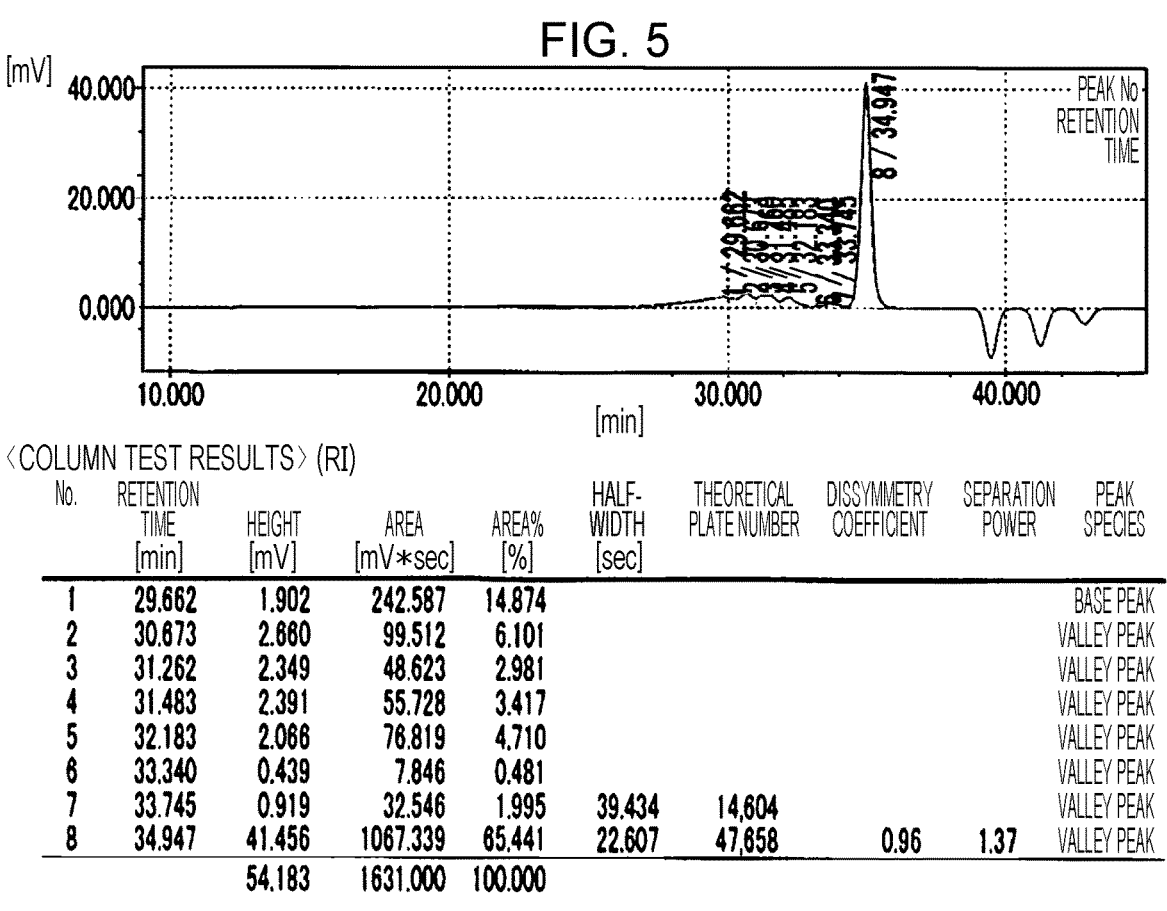

⟨COLUMN TEST RESULTS⟩ (RI)

| No. | RETENTION TIME [min] | HEIGHT [mV] | AREA [mV∗sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 29.662 | 1.902 | 242.587 | 14.874 | | | | | BASE PEAK |
| 2 | 30.673 | 2.660 | 99.512 | 6.101 | | | | | VALLEY PEAK |
| 3 | 31.262 | 2.349 | 48.623 | 2.981 | | | | | VALLEY PEAK |
| 4 | 31.483 | 2.391 | 55.728 | 3.417 | | | | | VALLEY PEAK |
| 5 | 32.183 | 2.066 | 76.819 | 4.710 | | | | | VALLEY PEAK |
| 6 | 33.340 | 0.439 | 7.846 | 0.481 | | | | | VALLEY PEAK |
| 7 | 33.745 | 0.919 | 32.546 | 1.995 | 39.434 | 14,604 | | | VALLEY PEAK |
| 8 | 34.947 | 41.456 | 1067.339 | 65.441 | 22.607 | 47,658 | 0.96 | 1.37 | VALLEY PEAK |
| | | 54.183 | 1631.000 | 100.000 | | | | | |

FIG. 6

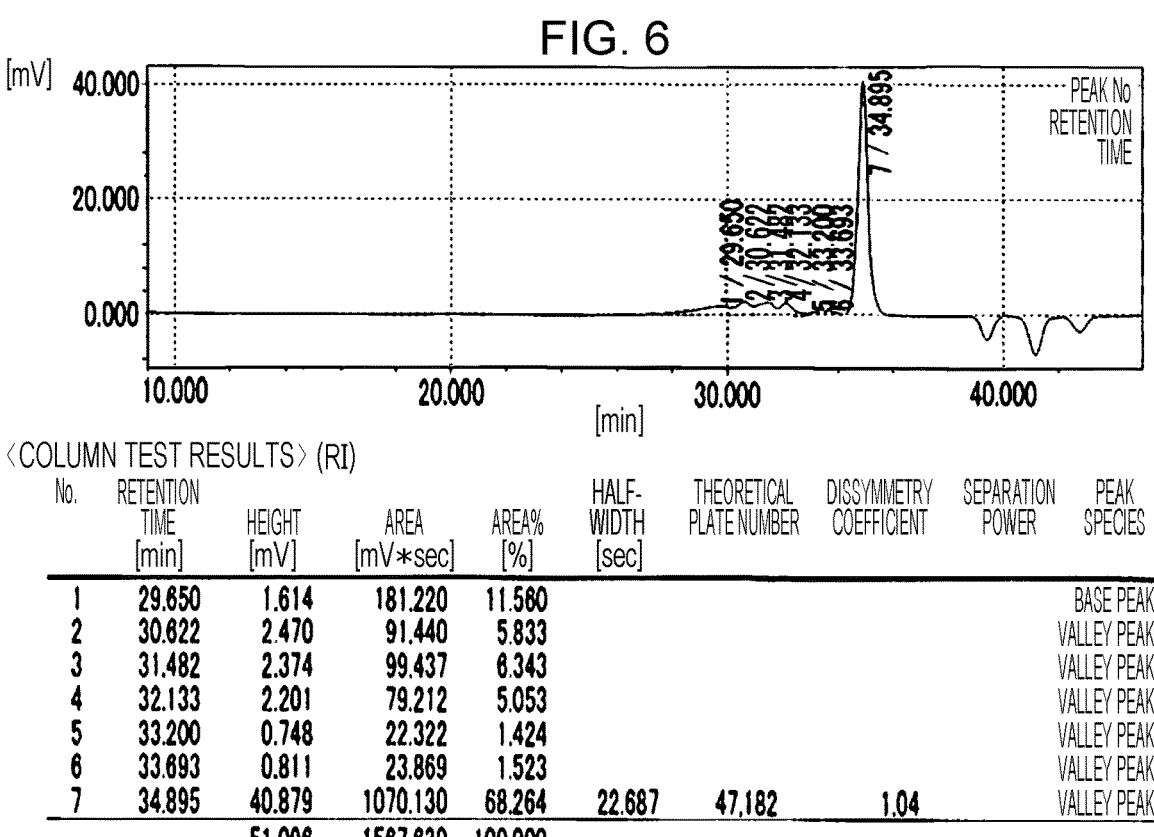

⟨COLUMN TEST RESULTS⟩ (RI)

| No. | RETENTION TIME [min] | HEIGHT [mV] | AREA [mV∗sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 29.650 | 1.614 | 181.220 | 11.560 | | | | | BASE PEAK |
| 2 | 30.622 | 2.470 | 91.440 | 5.833 | | | | | VALLEY PEAK |
| 3 | 31.482 | 2.374 | 99.437 | 6.343 | | | | | VALLEY PEAK |
| 4 | 32.133 | 2.201 | 79.212 | 5.053 | | | | | VALLEY PEAK |
| 5 | 33.200 | 0.748 | 22.322 | 1.424 | | | | | VALLEY PEAK |
| 6 | 33.693 | 0.811 | 23.869 | 1.523 | | | | | VALLEY PEAK |
| 7 | 34.895 | 40.879 | 1070.130 | 68.264 | 22.687 | 47,182 | 1.04 | | VALLEY PEAK |
| | | 51.096 | 1567.630 | 100.000 | | | | | |

FIG. 7

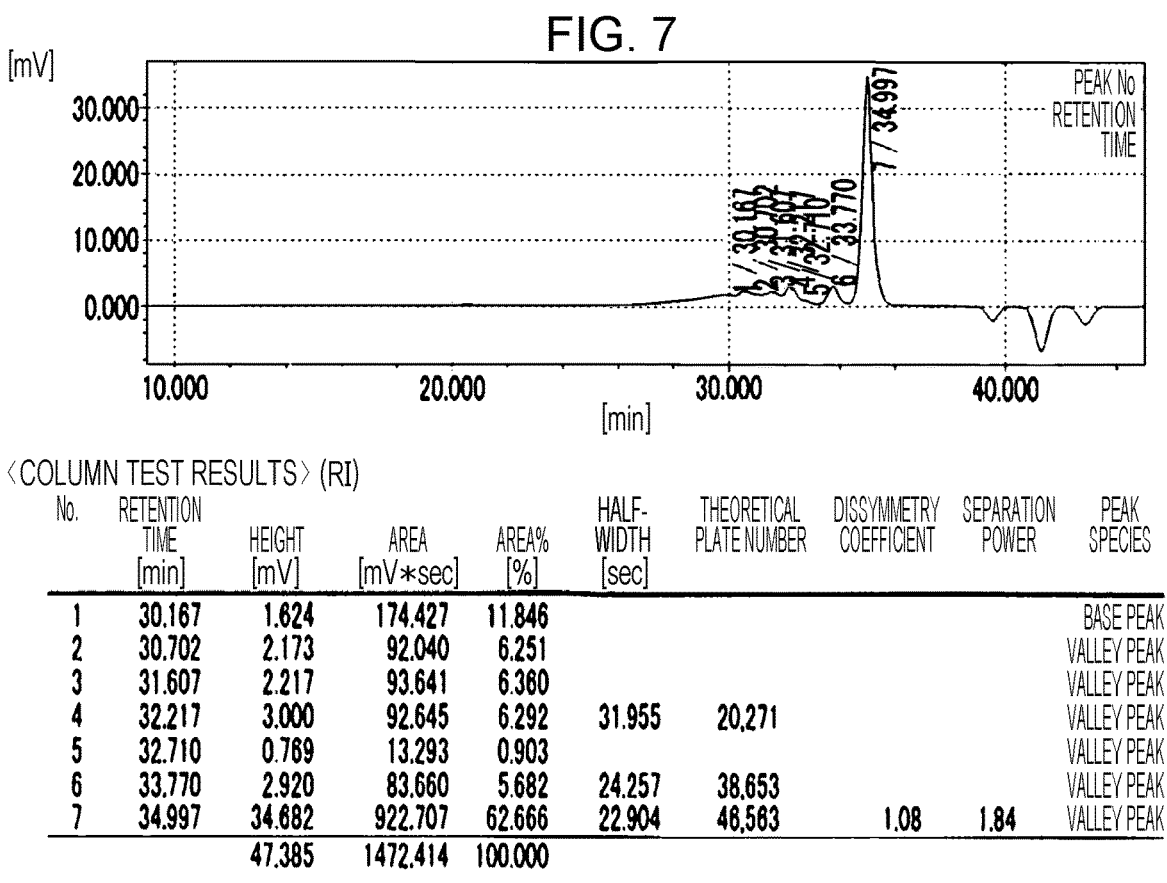

⟨COLUMN TEST RESULTS⟩ (RI)

| No. | RETENTION TIME [min] | HEIGHT [mV] | AREA [mV∗sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 30.167 | 1.624 | 174.427 | 11.846 | | | | | BASE PEAK |
| 2 | 30.702 | 2.173 | 92.040 | 6.251 | | | | | VALLEY PEAK |
| 3 | 31.607 | 2.217 | 93.641 | 6.360 | | | | | VALLEY PEAK |
| 4 | 32.217 | 3.000 | 92.645 | 6.292 | 31.955 | 20,271 | | | VALLEY PEAK |
| 5 | 32.710 | 0.769 | 13.293 | 0.903 | | | | | VALLEY PEAK |
| 6 | 33.770 | 2.920 | 83.660 | 5.682 | 24.257 | 38,653 | | | VALLEY PEAK |
| 7 | 34.997 | 34.682 | 922.707 | 62.666 | 22.904 | 46,563 | 1.08 | 1.84 | VALLEY PEAK |
| | | 47.385 | 1472.414 | 100.000 | | | | | |

FIG. 8

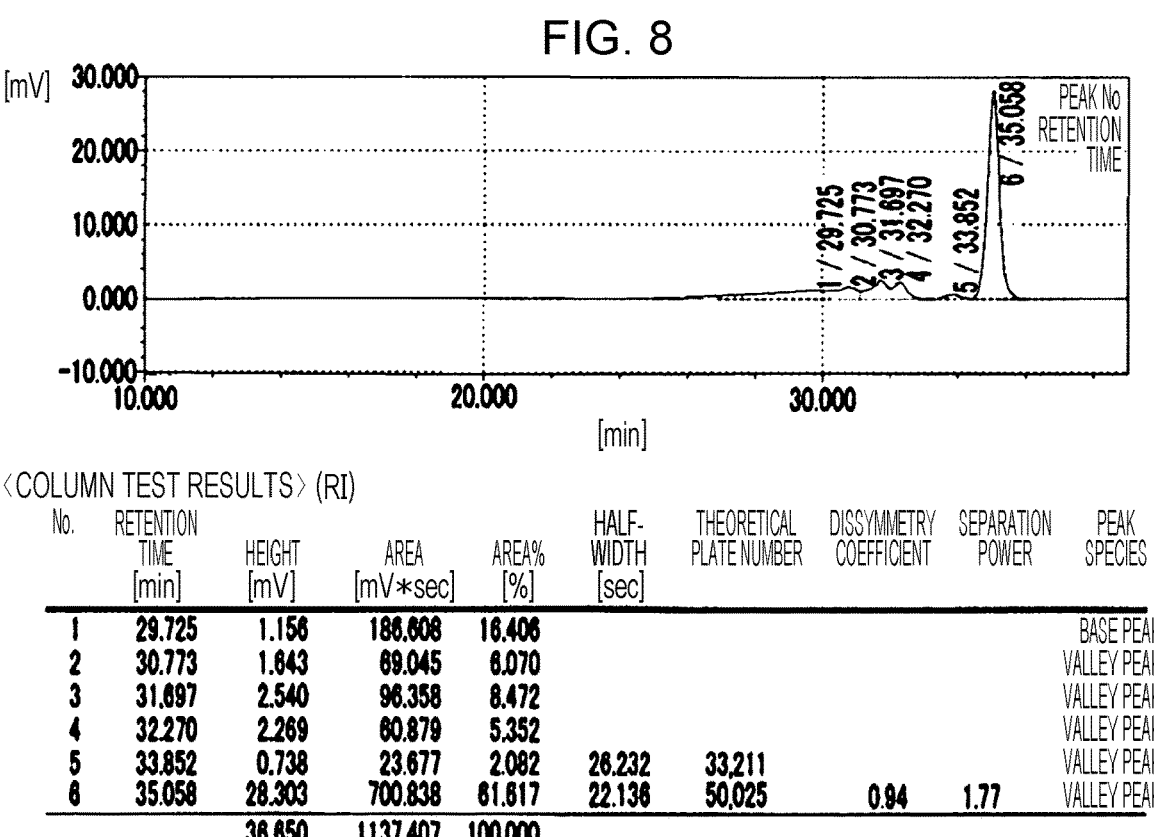

⟨COLUMN TEST RESULTS⟩ (RI)

| No. | RETENTION TIME [min] | HEIGHT [mV] | AREA [mV∗sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 29.725 | 1.156 | 186.608 | 16.406 | | | | | BASE PEAK |
| 2 | 30.773 | 1.643 | 69.045 | 6.070 | | | | | VALLEY PEAK |
| 3 | 31.697 | 2.540 | 96.358 | 8.472 | | | | | VALLEY PEAK |
| 4 | 32.270 | 2.269 | 60.879 | 5.352 | | | | | VALLEY PEAK |
| 5 | 33.852 | 0.738 | 23.677 | 2.082 | 26.232 | 33,211 | | | VALLEY PEAK |
| 6 | 35.058 | 28.303 | 700.838 | 61.617 | 22.136 | 50,025 | 0.94 | 1.77 | VALLEY PEAK |
| | | 36.650 | 1137.407 | 100.000 | | | | | |

FIG. 9

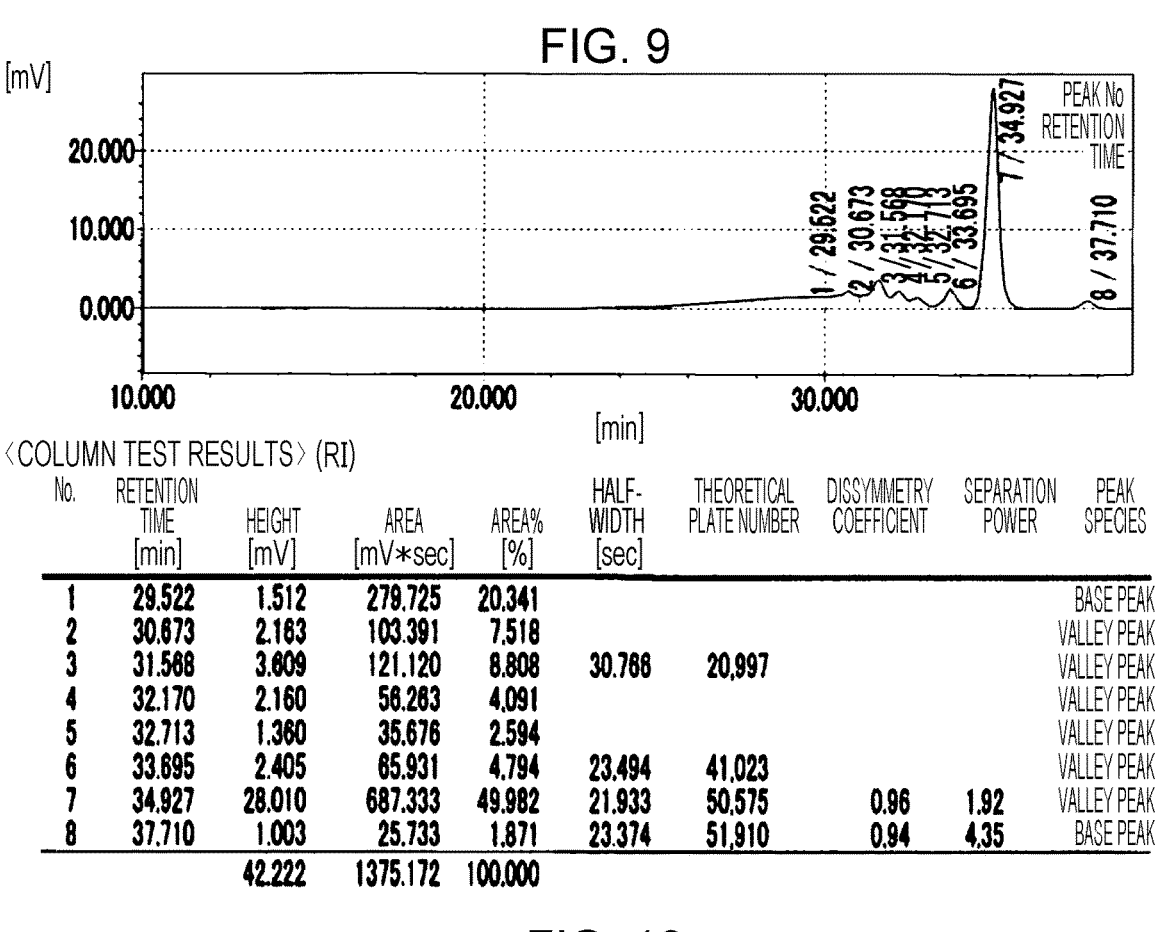

〈COLUMN TEST RESULTS〉 (RI)

| No. | RETENTION TIME [min] | HEIGHT [mV] | AREA [mV*sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 29.522 | 1.512 | 279.725 | 20.341 | | | | | BASE PEAK |
| 2 | 30.673 | 2.163 | 103.391 | 7.518 | | | | | VALLEY PEAK |
| 3 | 31.568 | 3.609 | 121.120 | 8.808 | 30.766 | 20,997 | | | VALLEY PEAK |
| 4 | 32.170 | 2.160 | 56.263 | 4.091 | | | | | VALLEY PEAK |
| 5 | 32.713 | 1.360 | 35.676 | 2.594 | | | | | VALLEY PEAK |
| 6 | 33.695 | 2.405 | 65.931 | 4.794 | 23.494 | 41,023 | | | VALLEY PEAK |
| 7 | 34.927 | 28.010 | 687.333 | 49.982 | 21.933 | 50,575 | 0.96 | 1.92 | VALLEY PEAK |
| 8 | 37.710 | 1.003 | 25.733 | 1.871 | 23.374 | 51,910 | 0.94 | 4.35 | BASE PEAK |
| | | 42.222 | 1375.172 | 100.000 | | | | | |

FIG. 10

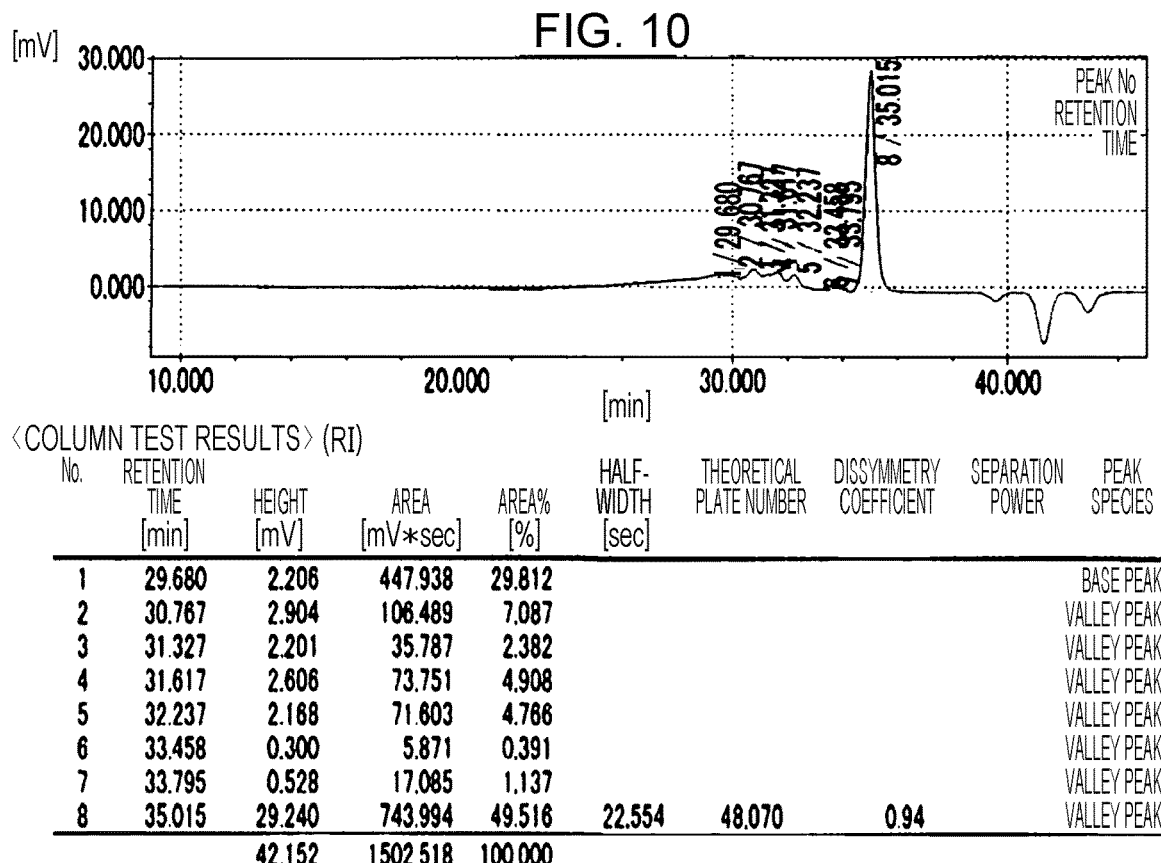

〈COLUMN TEST RESULTS〉 (RI)

| No. | RETENTION TIME [min] | HEIGHT [mV] | AREA [mV*sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 29.680 | 2.206 | 447.938 | 29.812 | | | | | BASE PEAK |
| 2 | 30.767 | 2.904 | 106.489 | 7.087 | | | | | VALLEY PEAK |
| 3 | 31.327 | 2.201 | 35.787 | 2.382 | | | | | VALLEY PEAK |
| 4 | 31.617 | 2.606 | 73.751 | 4.908 | | | | | VALLEY PEAK |
| 5 | 32.237 | 2.168 | 71.603 | 4.766 | | | | | VALLEY PEAK |
| 6 | 33.458 | 0.300 | 5.871 | 0.391 | | | | | VALLEY PEAK |
| 7 | 33.795 | 0.528 | 17.085 | 1.137 | | | | | VALLEY PEAK |
| 8 | 35.015 | 29.240 | 743.994 | 49.516 | 22.554 | 48,070 | 0.94 | | VALLEY PEAK |
| | | 42.152 | 1502.518 | 100.000 | | | | | |

FIG. 11

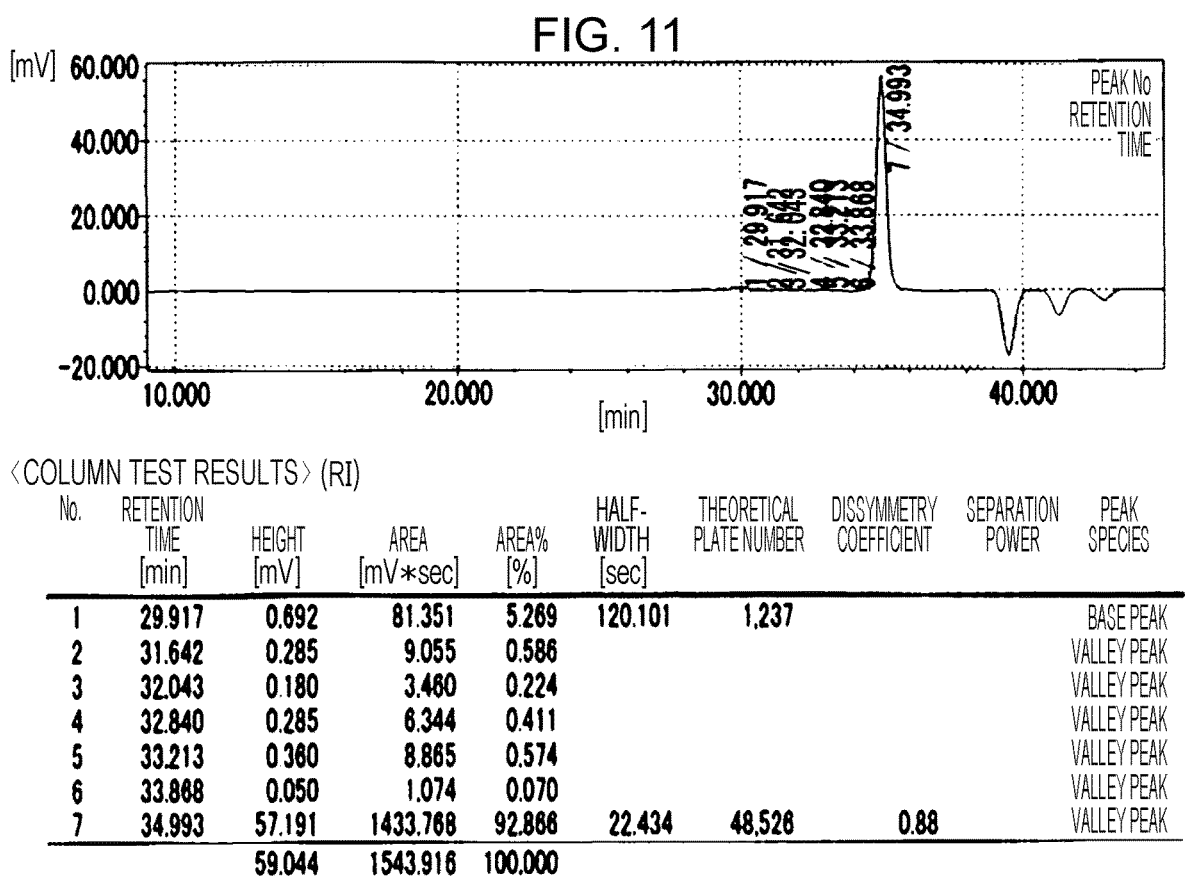

⟨COLUMN TEST RESULTS⟩ (RI)

| No. | RETENTION TIME [min] | HEIGHT [mV] | AREA [mV∗sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 29.917 | 0.692 | 81.351 | 5.269 | 120.101 | 1,237 | | | BASE PEAK |
| 2 | 31.642 | 0.285 | 9.055 | 0.586 | | | | | VALLEY PEAK |
| 3 | 32.043 | 0.180 | 3.460 | 0.224 | | | | | VALLEY PEAK |
| 4 | 32.840 | 0.285 | 6.344 | 0.411 | | | | | VALLEY PEAK |
| 5 | 33.213 | 0.360 | 8.865 | 0.574 | | | | | VALLEY PEAK |
| 6 | 33.868 | 0.050 | 1.074 | 0.070 | | | | | VALLEY PEAK |
| 7 | 34.993 | 57.191 | 1433.768 | 92.866 | 22.434 | 48,526 | 0.88 | | VALLEY PEAK |
| | | 59.044 | 1543.916 | 100.000 | | | | | |

FIG. 12

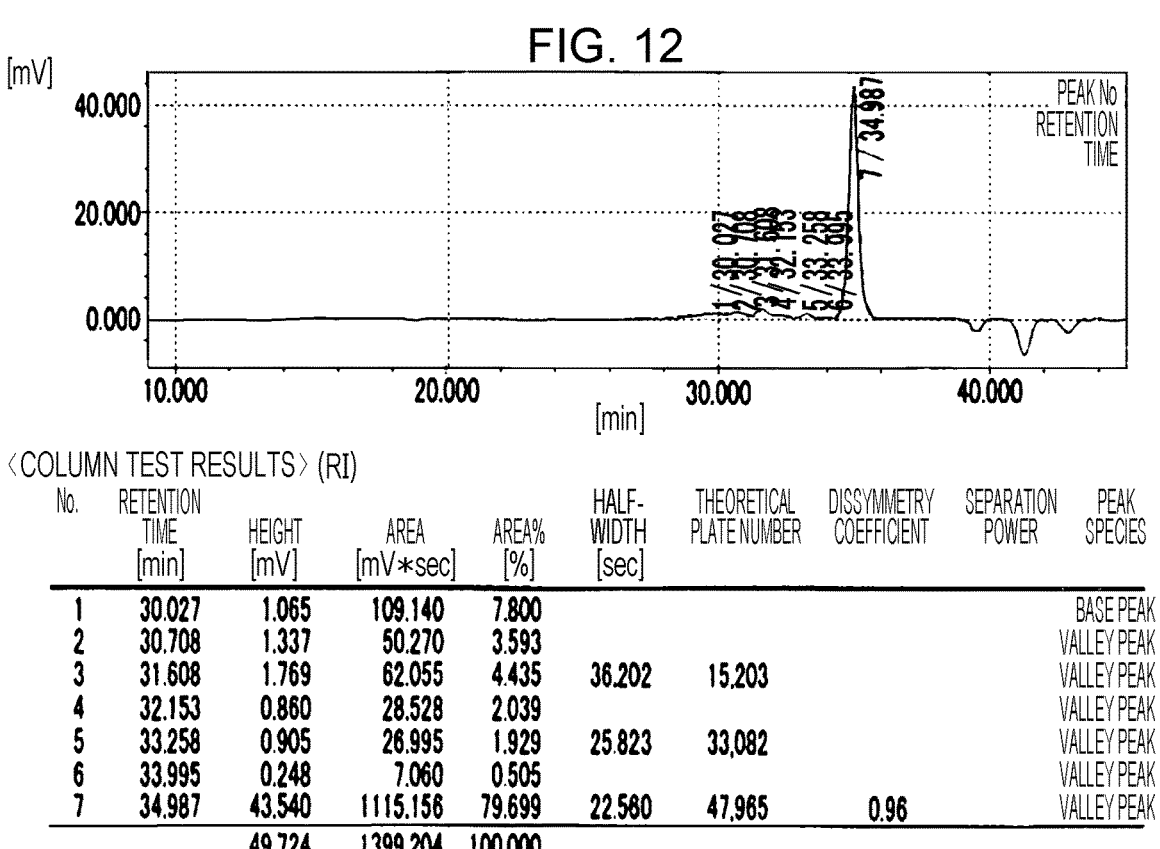

⟨COLUMN TEST RESULTS⟩ (RI)

| No. | RETENTION TIME [min] | HEIGHT [mV] | AREA [mV∗sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 30.027 | 1.065 | 109.140 | 7.800 | | | | | BASE PEAK |
| 2 | 30.708 | 1.337 | 50.270 | 3.593 | | | | | VALLEY PEAK |
| 3 | 31.608 | 1.769 | 62.055 | 4.435 | 36.202 | 15,203 | | | VALLEY PEAK |
| 4 | 32.153 | 0.860 | 28.528 | 2.039 | | | | | VALLEY PEAK |
| 5 | 33.258 | 0.905 | 26.995 | 1.929 | 25.823 | 33,082 | | | VALLEY PEAK |
| 6 | 33.995 | 0.248 | 7.060 | 0.505 | | | | | VALLEY PEAK |
| 7 | 34.987 | 43.540 | 1115.156 | 79.699 | 22.560 | 47,965 | 0.96 | | VALLEY PEAK |
| | | 49.724 | 1399.204 | 100.000 | | | | | |

⟨COLUMN TEST RESULTS⟩ (RI)

| No. | RETENTION TIME [min] | HEIGHT [mV] | AREA [mV∗sec] | AREA% [%] | HALF-WIDTH [sec] | THEORETICAL PLATE NUMBER | DISSYMMETRY COEFFICIENT | SEPARATION POWER | PEAK SPECIES |
|---|---|---|---|---|---|---|---|---|---|
| 1 | 30.028 | 0.822 | 73.717 | 4.921 | | | | | BASE PEAK |
| 2 | 30.695 | 0.950 | 37.293 | 2.489 | | | | | VALLEY PEAK |
| 3 | 31.640 | 1.010 | 34.367 | 2.294 | 44.023 | 10,302 | | | VALLEY PEAK |
| 4 | 32.197 | 0.635 | 19.388 | 1.294 | | | | | VALLEY PEAK |
| 5 | 33.277 | 0.381 | 9.508 | 0.635 | 23.372 | 40,429 | | | VALLEY PEAK |
| 6 | 34.043 | 0.316 | 9.622 | 0.642 | | | | | VALLEY PEAK |
| 7 | 35.008 | 51.779 | 1314.215 | 87.725 | 22.541 | 48,108 | 0.93 | | VALLEY PEAK |
| | | 55.893 | 1498.111 | 100.000 | | | | | |

BENZOXAZINE COMPOUND-CONTAINING COMPOSITION, CURABLE RESIN COMPOSITION, AND CURED PRODUCT THEREOF

CROSS-REFERENCE TO RELATED APPLICATIONS

This application is the U.S. National Phase under 35 U.S.C. § 371 of International Application PCT/JP2021/040192, filed Nov. 1, 2021, which claims priority to Japanese Patent Application No. JP2020-184536, filed Nov. 4, 2020. The International Application was published under PCT Article 21(2) in a language other than English.

TECHNICAL FIELD

The present invention relates to a benzoxazine compound-containing composition, a curable resin composition, and a cured product thereof. Specifically, the invention relates to a benzoxazine compound-containing composition with a low melt viscosity, and a curable resin composition including the benzoxazine compound-containing composition with a low melt viscosity and a cured product thereof.

BACKGROUND ART

Benzoxazine compounds are known as thermosetting resin raw materials that, when heated, undergo ring-opening polymerization of a benzoxazine ring to cure without producing any volatile by-products, and are used as raw materials of a molded body that can be used as a material for an insulating substrate (PTL 1), a liquid crystal alignment agent (PTL 2), resin compositions for semiconductor sealing (PTLs 3 and 4), and the like.

Resin compositions containing a benzoxazine compound represented by general formula (1) below in the present invention are known to provide cured products with improved heat resistance (glass transition temperature: Tg) (PTL 5), and thus their use as sealing resins for semiconductors is being studied.

However, benzoxazine compounds represented by general formula (1) below in the present invention that are produced by methods described in, for example, PTLs 5 and 6 below have high melt viscosities, and when the benzoxazine compounds are handled at high temperature in order to reduce their melt viscosities, polymerization proceeds, which disadvantageously limits their applicability to transfer molding and compression molding, which are typical semiconductor sealing methods.

CITATION LIST

Patent Literature

PTL 1: Japanese Unexamined Patent Application Publication No. 2007-002064
PTL 2: Japanese Unexamined Patent Application Publication No. 2009-175684
PTL 3: Japanese Unexamined Patent Application Publication No. 2015-025120
PTL 4: Japanese Unexamined Patent Application Publication No. 2011-231196
PTL 5: Japanese Unexamined Patent Application Publication No. 2018-184533

PTL 6: Japanese Unexamined Patent Application Publication No. 2018-016684

SUMMARY OF INVENTION

Technical Problem

An object of the present invention is to provide a composition with a low melt viscosity containing a benzoxazine compound represented by general formula (1) below, and a curable resin composition including the composition and a cured product thereof.

Solution to Problem

To achieve the above object, the present inventors have conducted intensive studies and found that a benzoxazine compound-containing composition with a low melt viscosity can be obtained when the content of a compound group having a specific molecular weight is in a specific range, thereby completing the present invention.

The present invention is as follows.

1. A benzoxazine compound-containing composition containing a benzoxazine compound represented by general formula (1) below and a compound group (A) having a molecular weight in the range of 1,000 to 10,000, in which in a gel permeation chromatography measurement using a differential refractometer as a detector, a peak area of the compound group (A) is in the range of 0.1 area % to 15 area % relative to a peak area of all components detected, and the benzoxazine compound-containing composition has a melt viscosity at 100° C. in the range of 0.1 Pa·S to 4.5 Pa·S,

[Chem. 1]

(1)

(where each R independently represents a hydrogen atom or a methyl group).

2. The benzoxazine compound-containing composition according to 1., in which in the gel permeation chromatography measurement, a peak area of the benzoxazine compound represented by general formula (1) is in the range of 62 area % to 90 area % relative to the peak area of all components detected (provided that a sum total of the peak area of the benzoxazine compound represented by general formula (1), the peak area of the compound group (A), and a peak area of other components detected is 100 area %).

3. A curable resin composition including the benzoxazine compound-containing composition according to 1. or 2.

4. The curable resin composition according to 3., containing the benzoxazine compound-containing composition according to 1. or 2. and at least one selected from the group consisting of epoxy resins, benzoxazine compounds other than the benzoxazine compound represented by general formula (1), and novolac phenol resins.

5. A cured product obtained by curing the curable resin composition according to 3. or 4.

Advantageous Effects of Invention

According to the present invention, a benzoxazine compound-containing composition with a low melt viscosity that contains a benzoxazine compound represented by general formula (1) above and has a melt viscosity at 100° C. in the range of 0.1 Pa·S to 4.5 Pa·S is provided.

The benzoxazine compound-containing composition of the present invention, because of containing the benzoxazine compound represented by general formula (1) above that provides a cured product with improved heat resistance and having a low melt viscosity at a temperature at which polymerization does not proceed, has high workability, allows fillers and the like to be added at a higher rate when formed into a curable resin composition, greatly contributing to improvement in heat dissipation, and enables sealing of semiconductors having more precise structures, so that the benzoxazine compound-containing composition can be used in a wide range of applications and thus is very useful.

The benzoxazine compound-containing composition with a low melt viscosity, and the curable resin composition containing the composition and the cured product thereof in the present invention are suitable for use as resin raw materials for varnishes that can be applied to various substrates, prepregs impregnated with varnishes, print circuit boards, sealants for electronic components, electrical and electronic molded parts, automotive parts, laminated materials, paints, resist inks, and the like.

BRIEF DESCRIPTION OF DRAWINGS

FIG. 1 shows a chart of a gel permeation chromatography analysis in Example 1.

FIG. 2 shows a chart of a gel permeation chromatography analysis in Example 2.

FIG. 3 shows a chart of a gel permeation chromatography analysis in Example 3.

FIG. 4 shows a chart of a gel permeation chromatography analysis in Example 4.

FIG. 5 shows a chart of a gel permeation chromatography analysis in Example 5.

FIG. 6 shows a chart of a gel permeation chromatography analysis in Example 6.

FIG. 7 shows a chart of a gel permeation chromatography analysis in Example 7.

FIG. 8 shows a chart of a gel permeation chromatography analysis in Comparative Example 1.

FIG. 9 shows a chart of a gel permeation chromatography analysis in Comparative Example 2.

FIG. 10 shows a chart of a gel permeation chromatography analysis in Comparative Example 3.

FIG. 11 shows a chart of a gel permeation chromatography analysis in Comparative Example 4.

FIG. 12 shows a chart of a gel permeation chromatography analysis in Example 8.

DESCRIPTION OF EMBODIMENTS

Figure 13:
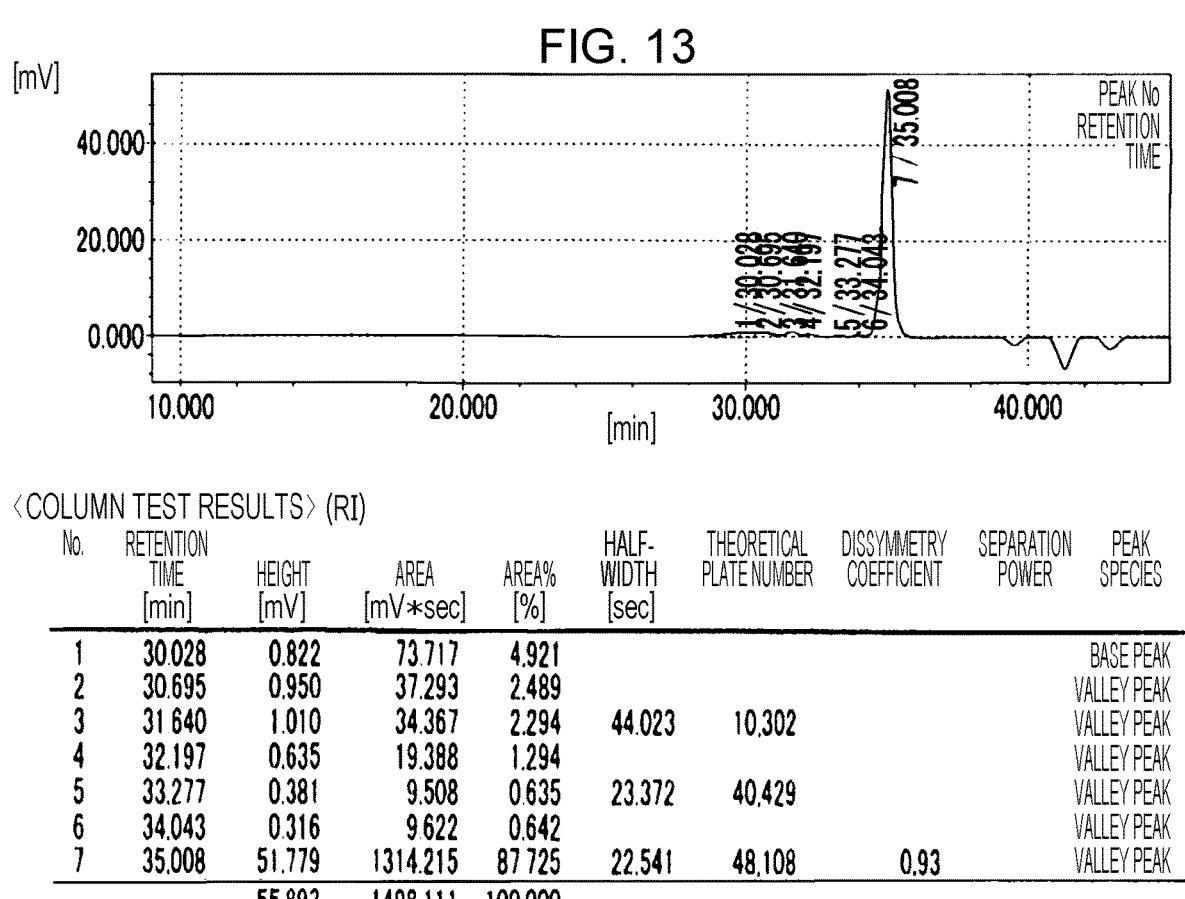
FIG. 13 shows a chart of a gel permeation chromatography analysis in Example 9.

A benzoxazine compound-containing composition of the present invention contains a benzoxazine compound represented by general formula (1) below.

[Chem. 2]

(1)

(In the formula, each R independently represents a hydrogen atom or a methyl group.)

Specific examples of the benzoxazine compound represented by general formula (1) above include compound (1a), compound (1b), and compound (1c) exemplified by the following chemical structures.

[Chem. 3]

(1a)

[Chem. 4]

(1b)

[Chem. 5]

(1c)

The benzoxazine compound in the present invention represented by general formula (1) can be produced by a method in which 3,4'-diaminodiphenyl ether, one or more phenol compounds selected from phenol, p-cresol, o-cresol, and m-cresol, and a formaldehyde selected from an aqueous formaldehyde solution, 1,3,5-trioxane, paraformaldehyde, and the like are allowed to undergo dehydration condensation reaction to cyclize, as shown by the following reaction formula.

[Chem. 6]

(In the formula, each R independently represents a hydrogen atom or a methyl group.)

The composition with a low melt viscosity in the present invention containing the benzoxazine compound represented by general formula (1) can be obtained by mixing 3,4'-diaminodiphenyl ether in the presence of a formaldehyde, a phenol compound, and a solvent over typically 1 to 10 hours, preferably 4 to 10 hours, more preferably 5 to 10 hours. Typically, 3,4'-diaminodiphenyl ether is mixed in the form of a solution in a phenol compound and/or a solvent. Adding 3,4'-diaminodiphenyl ether into the reaction system over time enables the content of a compound group (A) having a molecular weight in the range of 1,000 to 10,000 to be in a specific range.

The amount of the phenol compound used in the above reaction is in the range of 2.0 to 10.0 mol, preferably in the range of 2.0 to 8.0 mol, more preferably in the range 2.0 to 6.0 mol, relative to 1 mol of 3,4'-diaminodiphenyl ether.

The amount of the formaldehyde used in the above reaction is in the range of 4.0 to 20.0 mol, preferably in the range of 4.0 to 16.0 mol, more preferably in the range of 4.0 to 12.0 mol, relative to 1 mol of 3,4'-diaminodiphenyl ether.

The reaction is typically carried out in the presence of a solvent. The solvent is not particularly limited as long as it does not inhibit the reaction, and preferred examples include toluene, xylene, ethyl acetate, butyl acetate, chloroform, dichloromethane, tetrahydrofuran, and dioxane. These solvents can be used alone or in combination. The amount of solvent used is not particularly limited as long as the reaction is not hindered, and is typically in the range of 3 to 10 times, preferably in the range of 4 to 6 times the amount of 3,4'-diaminodiphenyl ether on a weight basis.

The reaction temperature is typically in the range of 70° C. to 100° C., preferably in the range of 75° C. to 90° C. The reaction may be carried out under normal pressure conditions, or may be carried out under increased pressure or reduced pressure.

A catalyst for accelerating the reaction is not particularly necessary, but an acid catalyst or a base catalyst can be used as needed. In this case, examples of acid catalysts that can be used include, but are not limited to, concentrated hydrochloric acid, hydrochloric acid gas, trifluoroacetic acid, methanesulfonic acid, p-toluenesulfonic acid, benzoic acid, and mixtures thereof, and examples of base catalysts that can be used include, but are not limited to, sodium hydroxide, sodium carbonate, triethylamine, triethanolamine, and mixtures thereof.

In another embodiment, a process of removing water derived from the raw materials or water generated during the reaction out of the system may be included. The process of removing water generated from a reaction solution is not particularly limited and can be performed by distilling the generated water azeotropically with the solvent system in the reaction solution. The generated water can be removed out of the reaction system by using, for example, an isobaric dropping funnel equipped with a cock, a Dimroth condenser, or a Dean-Stark apparatus.

From the final reaction mixture thus obtained, the benzoxazine compound-containing composition of the present invention can be obtained by a known method. For example, the benzoxazine compound-containing composition of the present invention can be obtained as follows: an aqueous sodium hydroxide solution, an aqueous potassium hydroxide solution, or an aqueous solution in which a basic compound such as sodium carbonate or potassium carbonate is dissolved is added to the final reaction solution, and stirring is performed (neutralization step); the resulting mixture is allowed to stand, and an aqueous layer is separated and removed from an organic solvent layer, after which an operation (water washing step) including addition of water to the organic solvent layer, stirring, standing, and separation and removal of an aqueous layer is performed multiple times to thoroughly wash the organic solvent layer; and the organic solvent layer washed with water is then distilled (distillation step) to remove the solvent and the phenol compound. The neutralization step, the water washing step, and the distillation step are preferably performed at temperatures ranging from 0° C. to 50° C., 0° C. to 90° C., and 50° C. to 100° C., respectively.

The benzoxazine compound-containing composition of the present invention has a melt viscosity at 100° C. in the range of 0.1 Pa·S to 4.5 Pa·S.

The melt viscosity in the present invention means a numerical value determined by measuring 15 g of a benzoxazine compound-containing composition by using a Brookfield viscometer under the following measurement conditions.

[Measurement Conditions]

Molten liquid temperature: 100° C.

Measurement time: within 15 minutes after complete dissolution of composition

Time required for complete dissolution: about 1 hour at oil bath temperature of 100° C. (±5° C.)

Number of revolutions: 6.0 rpm

The melt viscosity at 100° C. of the benzoxazine compound-containing composition of the present invention is preferably in the range of 0.5 Pa·S to 4.0 Pa·S, more preferably in the range of 0.5 Pa·S to 3.5 Pa·S.

When the benzoxazine compound according to the present invention is heated at a temperature higher than 100° C., the decrease of the benzoxazine compound due to the progress of polymerization and the increase of high-molecular-weight components such as the compound group (A) rapidly proceed. However, the benzoxazine compound-containing composition of the present invention is very useful because it has a low melt viscosity at a temperature at which such polymerization does not proceed.

The benzoxazine compound-containing composition of the present invention contains the compound group (A) having a molecular weight in the range of 1,000 to 10,000 such that in a gel permeation chromatography measurement using a differential refractometer as a detector, a peak area of the compound group (A) is in the range of 0.1 area % to 15 area % relative to a peak area of all components detected.

When the benzoxazine compound represented by general formula (1) above and the compound group (A) are compared with each other for their peak intensities normalized to the peak near 2850 cm$^{-1}$, which indicates benzene ring C—H stretch, in an analysis by infrared spectroscopy (IR), the compound group (A) has a weaker peak intensity near 3000 cm$^{-1}$.

The peak area of the compound group (A) is preferably in the range of 0.1 area % to 14 area %, more preferably in the range of 0.1 area % to 13 area %, particularly preferably 0.1 area % to 12 area %, relative to the peak area of all components detected.

The benzoxazine compound-containing composition of the present invention may contain the benzoxazine compound represented by general formula (1) above such that in the gel permeation chromatography measurement, the peak area of the benzoxazine compound is in the range of 62 area % to 82 area % relative to the peak area of all components detected, preferably in the range of 62 area % to 90 area % relative to the peak area of all components detected, provided that a sum total of the peak area of the benzoxazine compound represented by general formula (1), the peak area of the compound group (A), and a peak area of other components detected is 100 area %. The peak area of the benzoxazine compound represented by general formula (1) is more preferably in the range of 64 area % to 90 area %, still more preferably in the range of 65 area % to 90 area %, relative to the peak area of all components detected.

The gel permeation chromatography measurement of the benzoxazine compound-containing composition of the present invention using a differential refractometer as a detector means numerical values determined under the following measurement conditions.

[Measurement Conditions]
Flow rate: 1 mL/min
Eluent: tetrahydrofuran
Temperature: 40° C.
Wavelength: 254 nm
Sampling pitch: 100 msec
Measurement sample: 600-fold diluted solution of 10 mg of benzoxazine compound-containing composition in tetrahydrofuran
Injection volume: 20 μL

[Column] (From upstream, the following columns or their equivalents are used.)
TSKgel Guard Column HXL-L (manufactured by Tosoh Corporation)
TSKgel G4000HXL (manufactured by Tosoh Corporation) (filler: styrene divinylbenzene polymer, exclusion limit: 4×10$^5$, theoretical plate number: 16000, catalog value)
TSKgel G3000HXL (manufactured by Tosoh Corporation) (filler: styrene divinylbenzene polymer, exclusion limit: 6×10$^4$, theoretical plate number: 16000, catalog value)

TSKgel G2000HXL (manufactured by Tosoh Corporation) (filler: styrene divinylbenzene polymer, exclusion limit: 1×10$^4$, theoretical plate number: 16000, catalog value), two

[Molecular Weight Calculation Method]

Molecular weights in terms of standard polystyrene are calculated using a calibration curve that is a third-order approximation curve constructed using polystyrene standard samples.

In another embodiment, the benzoxazine compound-containing composition of the present invention can be produced by mixing a composition containing the benzoxazine compound represented by general formula (1) that is obtained by a method known in the art or a benzoxazine compound-containing composition obtained by the method described above with crystals of the benzoxazine compound represented by general formula (1) that are obtained by a method described below such that the benzoxazine compound-containing composition of the present invention is provided.

This mixing may be performed by, for example, mixing the materials each being in a solid state and melting the mixture to obtain a homogeneous composition or mixing the materials each being in a molten state to obtain a homogeneous composition. To prevent deterioration due to the influence of oxygen, the mixing is preferably performed in an inert gas atmosphere such as nitrogen.

The method of obtaining the crystals of the benzoxazine compound represented by general formula (1) is a method in which a compound represented by general formula (2) obtained by reacting 3,4'-diaminodiphenyl ether with a 2-hydroxybenzaldehyde compound (3) is reduced with sodium borohydride or the like to produce a compound represented by general formula (4), which is then reacted with formalin to obtain the benzoxazine compound represented by general formula (1), as shown by the following reaction formula. The benzoxazine compound represented by general formula (1) obtained by this method can be obtained as high-purity crystals.

[Chem. 7]

(3)

(2)

9

-continued (4)

(1)

(In the formula, each R independently represents a hydrogen atom or a methyl group.)

The benzoxazine compound-containing composition of the present invention can be used in the form of a curable resin composition containing the benzoxazine compound-containing composition as an essential component.

Examples of such forms include curable resin compositions obtained by mixing the benzoxazine compound-containing composition of the present invention with an inorganic filler such as silicon oxide, aluminum oxide, magnesium oxide, boron nitride, aluminum nitride, silicon nitride, silicon carbide, hexagonal boron nitride, and the like, or a reinforcement fiber such as carbon fiber, glass fiber, organic fiber, boron fiber, steel fiber, aramid fiber, and the like.

Examples of other forms include curable resin compositions containing the benzoxazine compound-containing composition of the present invention as an essential component and containing other polymeric materials.

The polymeric materials constituting the curable resin composition of the present invention are not particularly limited, and raw materials of an epoxy resin, a phenol resin, a bismaleimide resin, and a benzoxazine compound other than the benzoxazine compound represented by general formula (1) can be contained.

Examples of the epoxy resin include ortho-cresol epoxy resins, biphenyl epoxy resins, biphenyl aralkyl epoxy resins, naphthalene epoxy resins, anthracene dihydride epoxy resins, and brominated novolac epoxy resins.

Examples of the phenol resin include novolac phenol resins and bisphenol resins, and examples of the bismaleimide resin include raw materials of bismaleimide resins having the following structure.

[Chem. 8]

10

-continued

Examples of the benzoxazine compound other than the benzoxazine compound represented by general formula (1) include benzoxazine compounds having structures represented by general formulae (A) to (C) below.

[Chem. 9]

(A)

(In the formula, Ra represents a divalent group having 1 to 30 carbon atoms (excluding diphenyl ether-3,4'-diyl), each Rb independently represents an optionally substituted monovalent group having 1 to 10 carbon atoms, and n represents 0 or 1.)

[Chem. 10]

(B)

(In the formula, Rc represents a divalent group having 1 to 30 carbon atoms, a direct bond, an oxygen atom, a sulfur atom, a carbonyl group, or a sulfonyl group, and each Rd independently represents a monovalent group having 1 to 10 carbon atoms.)

[Chem. 11]

(C)

(In the formula, each Re independently represents a monovalent group having 1 to 10 carbon atoms, and m represents 0 or 1.)

Ra in the benzoxazine compound having the structure represented by general formula (A) represents a divalent group having 1 to 30 carbon atoms excluding diphenyl ether-3,4'-diyl. Specific examples thereof include alkylene groups such as 1,2-ethylene, 1,4-butylene, and 1,6-hexylene; alkylene groups having a cyclic structure such as 1,4-cyclohexylene, dicyclopentadienylene, and adamantylene; and arylene groups such as 1,4-phenylene, 4,4'-biphenylene, diphenyl ether-4,4'-diyl, diphenyl ketone-4,4'-diyl, and diphenyl sulfone-4,4'-diyl.

Each Rb in the benzoxazine compound having the structure represented by general formula (A) independently represents a monovalent group having 1 to 10 carbon atoms. Specific examples thereof include alkyl groups such as a methyl group, an ethyl group, a propyl group, and a butyl group; alkenyl groups such as a vinyl group and an allyl group; alkynyl groups such as an ethynyl group and a propargyl group; and aryl groups such as a phenyl group and a naphthyl group, and these groups may further have a substituent such as an alkoxy group having 1 to 4 carbon atoms, an acyl group having 1 to 4 carbon atoms, a halogen atom, a carboxyl group, a sulfo group, an allyloxy group, a hydroxy group, or a thiol group.

Examples of the benzoxazine compound having the structure represented by general formula (A) include P-d type benzoxazine manufactured by Shikoku Chemicals Corporation, and JBZ-OP100N and JBZ-BP100N manufactured by JFE Chemical Corporation.

Rc in the benzoxazine compound having the structure represented by general formula (B) represents a divalent group having 1 to 30 carbon atoms, a direct bond, an oxygen atom, a sulfur atom, a carbonyl group, or a sulfonyl group. Examples of the divalent group having 1 to 30 carbon atoms include alkylene groups such as methylene, 1,2-ethylene, 1,4-butylene, and 1,6-hexylene; alkylene groups having a cyclic structure such as 1,4-cyclohexylene, dicyclopentadienylene, and adamantylene; and alkylidene groups such as ethylidene, propylidene, isopropylidene, butylidene, phenylethylidene, cyclopentylidene, cyclohexylidene, cycloheptylidene, cyclododecylidene, 3,3,5-trimethylcyclohexylidene, and fluorenylidene.

Each Rd in the benzoxazine compound having the structure represented by general formula (B) independently represents a monovalent group having 1 to 10 carbon atoms. Specific examples thereof include alkyl groups such as a methyl group, an ethyl group, a propyl group, and a butyl group; alkenyl groups such as a vinyl group and an allyl group; alkynyl groups such as an ethynyl group and a propargyl group; and aryl groups such as a phenyl group and a naphthyl group, and these substituents may further have a substituent such as an alkoxy group having 1 to 4 carbon atoms, an acyl group having 1 to 4 carbon atoms, a halogen atom, a carboxyl group, a sulfo group, an allyloxy group, a hydroxy group, or a thiol group.

Examples of the benzoxazine compound having the structure represented by general formula (B) include F-a type benzoxazine manufactured by Shikoku Chemicals Corporation and BS-BXZ manufactured by Konishi Chemical Ind. Co., Ltd.

Each Re in the benzoxazine compound having the structure represented by general formula (C) independently represents a monovalent group having 1 to 10 carbon atoms. Specific examples thereof include alkyl groups such as a methyl group, an ethyl group, a propyl group, and a butyl group; alkenyl groups such as a vinyl group and an allyl group; alkynyl groups such as an ethynyl group and a propargyl group; and aryl groups such as a phenyl group and a naphthyl group, and these substituents may further have a substituent such as an alkoxy group having 1 to 4 carbon atoms, an acyl group having 1 to 4 carbon atoms, a halogen atom, a carboxyl group, a sulfo group, an allyloxy group, a hydroxy group, or a thiol group.

In particular, the curable resin composition of the present invention preferably contains the composition containing the benzoxazine compound represented by general formula (1) above and at least one selected from the group consisting of epoxy resins, benzoxazine compounds other than the benzoxazine compound represented by general formula (1), and novolac phenol resins.

In the curable resin composition of the present invention, the amount of the other polymeric materials mixed with the composition containing the benzoxazine compound represented by general formula (1) above is in the range of 0.01 parts by weight to 100 parts by weight relative to 1 part by weight of the composition containing the benzoxazine compound represented by general formula (1) above.

The curable resin composition of the present invention can be obtained by adding the composition containing the benzoxazine compound represented by general formula (1) above to the other optional polymeric materials described above. The method of the addition is not particularly limited, and a method known in the art can be employed. Examples of the method include addition during synthesis or polymerization of the polymeric materials, addition of a resin formed of the polymeric materials to a molten resin melted in, for example, a melt extrusion step, and infiltration into, for example, a resin product formed of the polymeric materials.

The curable resin composition of the present invention may entrain bubbles when cured if water or a residual solvent is contained in the composition, and thus to prevent this, it is preferable to perform a vacuum degassing treatment as a pretreatment. The vacuum degassing treatment may be performed at any temperature at which the resin composition of the present invention is in a molten state but is preferably performed at up to 140° C. because curing does not proceed and degassing is facilitated. The vacuum degassing treatment is preferably, but not necessarily, performed at a low pressure (highly reduced pressure) and may be performed either in air or in a nitrogen-purged atmosphere. The vacuum degassing treatment is performed until no bubbles can be visually observed.

The curable resin composition of the present invention can be used as a mixture with an inorganic filler such as silicon oxide, aluminum oxide, magnesium oxide, boron nitride, aluminum nitride, silicon nitride, silicon carbide, hexagonal boron nitride, and the like, or a reinforcement fiber such as carbon fiber, glass fiber, organic fiber, boron fiber, steel fiber, aramid fiber, and the like, depending on the need in the application.

Next, a cured product of the present invention will be described.

The cured product of the present invention can be obtained by curing the composition containing the benzoxazine compound represented by general formula (1) of the present invention or the curable resin composition of the present invention.

Examples of the method for producing the cured product of the present invention include curing by heating to a predetermined temperature; melting by heating, injecting into a mold or the like, and further heating the mold to achieve curing and molding; and injecting a melt into a preheated mold and curing the melt.

The cured product of the present invention can be cured by performing ring-opening polymerization under the same curing conditions as those for ordinary benzoxazines. The curing temperature is typically in a temperature range of 140° C. to 250° C., preferably in a temperature range of 160° C. to 220° C., more preferably in a temperature range of 160° C. to 200° C., and is particularly preferably in a temperature range of 180° C. to 200° C. in order to provide a cured product with improved mechanical properties. When curing is performed in such a temperature range, the reaction time may be about 2 to 10 hours.

The resin composition of the present invention can be cured by heat alone, but it is preferable to use a curing accelerator depending on, for example, the components other than the benzoxazine compound represented by general formula (1) above and the content thereof. Examples of curing accelerators that can be used include, but are not limited to, tertiary amines such as 1,8-diaza-bicyclo[5.4.0] undecene-7, triethylenediamine, and tris(2,4,6-dimethylaminomethyl) phenol; imidazoles such as 2-ethyl-4-methylimidazole and 2-methylimidazole; phosphorus compounds such as triphenylphosphine, tetraphenylphosphonium bromide, tetraphenylphosphonium tetraphenylborate, and tetra-n-butylphosphonium-O,O-diethyl phosphorodithioate; quaternary ammonium salts; organic metal salts; and derivatives thereof. These may be used alone or in combination. Among these curing accelerators, tertiary amines, imidazoles, and phosphorus compounds are preferably used.

EXAMPLES

The present invention will now be described more specifically with reference to Examples.

Values of physical properties in the following examples were determined by the following methods.

<Method of Analysis>

1. Melt Viscosity

Apparatus: Brookfield viscometer (TVB-10, rotor: THM-12/manufactured by Toki Sangyo Co., Ltd.)

[Measurement Conditions]

Sample volume: benzoxazine compound-containing composition, 15 g

Molten liquid temperature: 100° C.

Measurement time: within 15 minutes after complete dissolution of composition

Time required for complete dissolution: about 1 hour at oil bath temperature of 100° C. (±5° C.)

Number of revolutions: 6.0 rpm

2. Gel Permeation Chromatography

Apparatus: HLC-8320/manufactured by Tosoh Corporation

Detector: differential refractometer (RI)

[Measurement Conditions]

Flow rate: 1 mL/min

Eluent: tetrahydrofuran

Temperature: 40° C.

Wavelength: 254 nm

Sampling pitch: 100 msec

Measurement sample: 600-fold diluted solution of 10 mg of benzoxazine compound-containing composition in tetrahydrofuran Injection volume: 20 μL

[Column] (from upstream)

Guard Column HXL-L+G4000HXL+G3000HXL+G2000HXL×2 (7.8 mm ID×30 cm, manufactured by Tosoh Corporation)

[Molecular Weight Calculation Method]

Molecular weights in terms of standard polystyrene were calculated using a calibration curve that was a third-order approximation curve constructed using polystyrene standard samples below.

The measurement conditions were the same as the above measurement conditions except that only the injection volume was changed to 10 μL.

(Polystyrene Standard Samples)

TSKgel Standard Polystyrene A-500: Nominal Mol. Wt. 5.9×10² , Mw/Mn 1.19 (0005203/manufactured by Tosoh Corporation)

TSKgel Standard Polystyrene A-2500: Nominal Mol. Wt. 2.63×10³, Mw/Mn 1.05 (0005205/manufactured by Tosoh Corporation)

TSKgel Standard Polystyrene A-5000: Nominal Mol. Wt. 5.06×10³, Mw/Mn 1.02 (0005206/manufactured by Tosoh Corporation).

TSKgel Standard Polystyrene F-1: Nominal Mol. Wt. 1.02×10⁴, Mw/Mn 1.02 (0005207/manufactured by Tosoh Corporation)

TSKgel Standard Polystyrene F-2: Nominal Mol. Wt. 1.74×10⁴, Mw/Mn 1.01 (0005208/manufactured by Tosoh Corporation)

TSKgel Standard Polystyrene F-4: Nominal Mol. Wt. 3.79×10⁴, Mw/Mn 1.01 (0005209/manufactured by Tosoh Corporation)

Example 1

In a four-necked flask equipped with a thermometer, a stirrer, and a condenser, 547 g (16.8 mol) of 92 wt % paraformaldehyde, 3336 g of toluene, and 394 g (4.19 mol) of phenol were loaded, and after the reaction vessel was purged with nitrogen, a solution prepared by dissolving 839 g (4.19 mol) of 3,4'-diaminodiphenyl ether, 839 g of toluene, and 394 g (4.19 mol) of phenol at 70° C. was intermittently added dropwise over 6 hours at 80° C. (at this time, the molar ratio of 3,4'-diaminodiphenyl ether, phenol, and paraformaldehyde was 1:2:4). Thereafter, stirring was performed at 82° C. for 18 hours. The reaction solution was analyzed by gel permeation chromatography under the above conditions to show that the percentage of compound (1a) present in the reaction solution was 70.2 area %.

After completion of the reaction, 1800 g of a 3% aqueous sodium hydroxide solution was added at 30° C. with stirring, and after stirring for 30 minutes, the resulting mixture was allowed to stand, and an aqueous layer was separated and removed. Thereafter, 2200 g of water was added to an oil layer with stirring at 30° C., and after stirring for 30 minutes, the resulting mixture was allowed to stand, and an aqueous layer was separated and removed. The procedure from the addition of water to the extraction of an aqueous layer was repeated four times.

From the oil layer obtained, toluene and phenol were removed by distillation under reduced pressure. The temperature and pressure during the distillation were gradually increased and decreased, finally reaching 90° C. and 1.5 kPa, respectively. A molten liquid of the composition containing compound (1a) was extracted, solidified by cooling, and then pulverized to obtain 1383 g of a compound (1a)-containing composition.

From the results of ¹H-NMR and ¹³C-NMR analyses, the composition obtained was confirmed to contain compound (1a).

The compound (1a)-containing composition obtained was subjected to a gel permeation chromatography analysis using a differential refractometer as a detector under the above conditions, revealing that the peak area of compound (1a) relative to the peak area of all components detected (hereinafter referred to as the peak area percentage of compound (1a)) was 70.3 area %. The gel permeation chromatography analysis using a differential refractometer as a detector under the above conditions also revealed that the peak area of the compound group (A) having a molecular weight of 1,000 to 10,000 relative to the peak area of all components detected (hereinafter referred to as the peak area percentage of the compound group (A)) was 9.5 area %. A chart of this gel permeation chromatography analysis is shown in FIG. 1.

The melt viscosity at 100° C. of 15 g of the compound (1a)-containing composition obtained, as measured using a Brookfield viscometer (TVB-10/manufactured by Toki Sangyo Co., Ltd.) under the above measurement conditions, was 1.8 Pa·S.

Example 2

After the loading, reaction, and liquid separation steps were performed in the same manner as in Example 1, the distillation step was performed at a final temperature of 95° C. A molten liquid of the composition containing compound (1a) was extracted, solidified by cooling, and then pulverized to obtain 1280 g of a compound (1a)-containing composition.

The compound (1a)-containing composition obtained was subjected to a gel permeation chromatography analysis using a differential refractometer as a detector, revealing that the peak area percentage of compound (1a) was 69.0 area % and the peak area percentage of the compound group (A) was 11.3 area %. A chart of this gel permeation chromatography analysis is shown in FIG. 2.

The melt viscosity at 100° C. was 2.7 Pa·S.

Example 3

A compound (1a)-containing composition was obtained in the same manner as in Example 1 except that the solution was intermittently added dropwise over 4.5 hours.

The compound (1a)-containing composition obtained was subjected to a gel permeation chromatography analysis using a differential refractometer as a detector, revealing that the peak area percentage of compound (1a) was 69.4 area % and the peak area percentage of the compound group (A) was 9.4 area %. A chart of this gel permeation chromatography analysis is shown in FIG. 3.

The melt viscosity at 100° C. was 2.0 Pa·S.

Example 4

A compound (1a)-containing composition was obtained in the same manner as in Example 1 except that 3,4'-diaminodiphenyl ether, phenol, and paraformaldehyde were loaded at a molar ratio of 1:4:8.

The compound (1a)-containing composition obtained was subjected to a gel permeation chromatography analysis using a differential refractometer as a detector, revealing that the peak area percentage of compound (1a) was 72.8 area % and the peak area percentage of the compound group (A) was 8.0 area %. A chart of this gel permeation chromatography analysis is shown in FIG. 4.

The melt viscosity at 100° C. was 1.5 Pa·S.

Example 5

A compound (1a)-containing composition was obtained in the same manner as in Example 1 except that the solution was intermittently added dropwise over 1 hour.

The compound (1a)-containing composition obtained was subjected to a gel permeation chromatography analysis using a differential refractometer as a detector, revealing that the peak area percentage of compound (1a) was 65.4 area % and the peak area percentage of the compound group (A)

was 14.9 area %. A chart of this gel permeation chromatography analysis is shown in FIG. 5.

The melt viscosity at 100° C. was 2.2 Pa·S.

Example 6

A compound (1a)-containing composition was obtained in the same manner as in Example 1 except that the solution was intermittently added dropwise over 2 hours.

The compound (1a)-containing composition obtained was subjected to a gel permeation chromatography analysis using a differential refractometer as a detector, revealing that the peak area percentage of compound (1a) was 68.3 area % and the peak area percentage of the compound group (A) was 11.6 area %. A chart of this gel permeation chromatography analysis is shown in FIG. 6.

The melt viscosity at 100° C. was 2.0 Pa·S.

Example 7

A compound (1a)-containing composition was obtained in the same manner as in Example 1 except that reaction product water was removed by reducing the pressure in the reaction step after the intermittent dropwise addition.

The compound (1a)-containing composition obtained was subjected to a gel permeation chromatography analysis using a differential refractometer as a detector, revealing that the peak area percentage of compound (1a) was 62.7 area % and the peak area percentage of the compound group (A) was 11.8 area %. A chart of this gel permeation chromatography analysis is shown in FIG. 7.

The melt viscosity at 100° C. was 2.1 Pa·S.

Comparative Example 1: Production Method Described in PTL 5

In a four-necked flask equipped with a thermometer, a stirrer, and a condenser, 176.3 g of phenol, 150.0 g of 3,4'-diaminodiphenyl ether, and 750.0 g of toluene were loaded, and 257.1 g of a 35% aqueous formalin solution was added dropwise over 35 minutes with stirring at an internal temperature of 65° C. After completion of the dropwise addition, simple distillation was performed at 85° C. under normal pressure to distill out water and toluene, and the distilled toluene was returned to the flask. After 35.3 g of phenol was further added, the reaction was carried out at 86° C. for 2 hours under reflux.

After completion of the reaction, the internal temperature was lowered to room temperature, and 300 g of a 10% aqueous sodium hydroxide solution was added to the reaction mixture solution. Stirring was performed for 20 minutes, and an aqueous layer was separated and removed. To the oil layer obtained, 200 g of toluene was added, and 800 g of a 3.75% aqueous sodium hydroxide solution was then added. The resulting mixture was stirred for 20 minutes and allowed to stand, and an aqueous layer was separated and removed.

Subsequently, a washing operation including addition of 300 g of water to the oil layer obtained, stirring, and removal of an aqueous layer was repeated six times. From the washed oil layer, toluene was distilled off under reduced pressure to obtain 185.1 g of a compound (1a)-containing composition.

The compound (1a)-containing composition obtained was subjected to a gel permeation chromatography analysis using a differential refractometer as a detector, revealing that the peak area percentage of compound (1a) was 61.6 area % and the peak area percentage of the compound group (A)

was 16.4 area %. A chart of this gel permeation chromatography analysis is shown in FIG. 8.

The melt viscosity at 100° C. was 4.7 Pa·S.

Comparative Example 2: Production Method Described in PTL 6

In a four-necked flask equipped with a thermometer, a stirrer, and a condenser, 52.5 g of 3,4'-diaminodiphenyl ether, 49.5 g of phenol, 34.5 g of 92% paraformaldehyde, and 250 g of toluene were loaded and allowed to react at 90° C. while performing dehydration. Thereafter, the reaction product was heated to 110° C. to distill off toluene, after which remaining toluene and unreacted materials were removed by distillation under reduced pressure at 125° C., and then 118.2 g of a compound (1a)-containing composition was obtained.

The compound (1a)-containing composition obtained was subjected to a gel permeation chromatography analysis using a differential refractometer as a detector, revealing that the peak area percentage of compound (1a) was 50.0 area % and the peak area percentage of the compound group (A) was 20.3 area %. A chart of this gel permeation chromatography analysis is shown in FIG. 9.

The melt viscosity at 100° C. was 5.6 Pa·S.

Comparative Example 3

A compound (1a)-containing composition was obtained in the same manner as in Example 1 except that the solution was added in one portion.

The compound (1a)-containing composition obtained was subjected to a gel permeation chromatography analysis using a differential refractometer as a detector, revealing that the peak area percentage of compound (1a) was 49.5 area % and the peak area percentage of the compound group (A) was 29.8 area %. A chart of this gel permeation chromatography analysis is shown in FIG. 10.

The melt viscosity at 100° C. was 19.1 Pa·S.

Comparative Example 4

A compound (1a)-containing composition was obtained according to the following reaction formula and procedure.

[Chem. 12]

(3a)

(2a)

-continued (2a)

NaBH₄ →

(4a)

(4a)

(1a)

In a four-necked flask equipped with a thermometer, a stirrer, and a condenser, 127 g (0.64 mol) of 3,4'-diaminodiphenyl ether and 635 g of ethanol were loaded, and after the reaction vessel was purged with nitrogen, 168 g (1.38 mol) of 2-hydroxybenzaldehyde, i.e., a compound represented by formula (3a) above, was added dropwise at 40° C. over 30 minutes. Thereafter, 630 g of ethanol was added, and stirring was performed at 60° C. for 2 hours and at 78° C. under reflux for 8 hours. After completion of the reaction, a reaction solution containing a compound represented by formula (2a) above was cooled to 25° C., 1138 g of ethanol was added, and 53 g (1.39 mol) of sodium borohydride was intermittently added over 2 hours. Thereafter, stirring was performed at 25° C. for 7 hours. After completion of the reaction, 1510 g of water was added, and stirring was performed at 25° C. for 14 hours. The resulting slurry liquid was subjected to solid-liquid separation by filtration to obtain a solid. The solid obtained was washed with 300 g of a 30% aqueous methanol solution twice and with 500 g of water, and then dried at 50° C. under reduced pressure to obtain 280 g of a compound represented by formula (4a) as a solid. The purity determined by a gel permeation chromatography analysis using a differential refractometer as a detector was 96.9 area %.

In a four-necked flask, 280 g of the compound represented by general formula (4a), 2290 g of butyl acetate, 47 g (0.7 mol) of acetic acid, and 490 g of water were loaded, and the reaction vessel was purged with nitrogen. After stirring at 70° C. for 2 hours, the resulting mixture was allowed to stand, and an aqueous layer was separated and removed. Thereafter, 500 g of water was added to the oil layer at 70° C. with stirring, and after stirring for 30 minutes, the resulting mixture was allowed to stand, and an aqueous layer was separated and removed. The procedure from the addition of water to the extraction of an aqueous layer was repeated four times. The pH of the oil layer at this time was 3.

The oil layer obtained was cooled to 40° C., and 207 g (2.4 mol) of 35% formalin was added dropwise over 30 minutes while maintaining 40° C., after which stirring was performed at 40° C. for 5 hours. Thereafter, butyl acetate was partially distilled off at 90° C. under reduced pressure to a solids concentration of 50%. The oil layer obtained was gradually cooled to 25° C., and precipitated crystals were filtered. The resulting crystals were dried by raising the temperature to 60° C. under reduced pressure to obtain 190 g of a compound (1a)-containing composition. The yield relative to 3,4'-diaminodiphenyl ether was 68%.

From the results of 1H-NMR and 13C-NMR analyses, the composition obtained was confirmed to contain compound (1a).

1H-NMR (400 MHZ) measurement (solvent: CDCl3): 4.64 (s, 2H: a), 4.66 (s, 2H: a), 5.37 (s, 2H: b), 5.39 (s, 2H: b), 6.53-6.55 (ddd, 1H: c), 6.81-7.35 (m, 15H: others). 13C-NMR (400 MHZ) measurement (solvent: CDCl3): 50.28 (A), 50.36 (A), 79.21 (B), 80.14 (B), 108.15 (H), 110.60 (I), 112.23 (J), 114.69 (C), 117.06 (K), 120.20 (L), 120.96 (M), 126.85 (N), 127.97 (O), 128.33 (P), 129.14 (Q), 130.20 (R), 149.90 (D), 151.27 (E), 154.38 (F), 159.06 (G).

The compound (1a)-containing composition obtained was subjected to a gel permeation chromatography analysis using a differential refractometer as a detector, revealing that the peak area percentage of compound (1a) was 92.9 area % and the peak area percentage of the compound group (A) was 5.3 area %. A chart of this gel permeation chromatography analysis is shown in FIG. 11.

The compound (1a)-containing composition obtained was heated to 100° C. in order to measure the melt viscosity at 100° C., but did not melt.

Example 8

A compound (1a)-containing composition obtained in the same manner as in Example 3 and the compound (1a)-containing composition obtained in Comparative Example 4 were melt-mixed to obtain a compound (1a)-containing composition.

The compound (1a)-containing composition obtained was subjected to a gel permeation chromatography analysis using a differential refractometer as a detector, revealing that the peak area percentage of compound (1a) was 79.7 area % and the peak area percentage of the compound group (A) was 7.8 area %. A chart of this gel permeation chromatography analysis is shown in FIG. 12.

The melt viscosity at 100° C. was 1.4 Pa·S.

Example 9

A compound (1a)-containing composition obtained in the same manner as in Example 3 and the compound (1a)-containing composition obtained in Comparative Example 4 were melt-mixed at a weight ratio different from that in Example 8 to obtain a compound (1a)-containing composition.

The compound (1a)-containing composition obtained was subjected to a gel permeation chromatography analysis using a differential refractometer as a detector, revealing that the peak area percentage of compound (1a) was 87.7 area % and the peak area percentage of the compound group (A) was 4.9 area %. A chart of this gel permeation chromatography analysis is shown in FIG. 13.

The melt viscosity at 100° C. was 1.1 Pa·S.

It has been revealed that the benzoxazine compound-containing compositions of Comparative Examples 1 to 3, which are not specific examples of the present invention, have high melt viscosities, and, for example, their applicability to transfer molding and compression molding, which are typical semiconductor sealing methods, is limited.

It has also been revealed that the benzoxazine compound-containing composition of Comparative Example 4, which is not a specific example of the present invention, does not melt at 100° C., and its applicability to various molding methods is further limited.

By contrast, it has been revealed that the benzoxazine compound-containing compositions of Examples 1 to 9, which are specific examples of the present invention, have significantly low melt viscosities at 100° C. because the peak area percentage of the compound group (A) is in a specific range. Thus, it has been revealed that the benzoxazine compound represented by general formula (1) that improves heat resistance has high workability, allows fillers and the like to be added at a higher rate, greatly contributing to improvement in heat dissipation, and enables sealing of semiconductors having more precise structures, and thus can be used in a wide range of applications and is very useful.

<Component Analysis of Compound (1a)-Containing Composition>

Using the compound (1a)-containing composition obtained in Example 3, GPC-FTIR analysis was performed to analyze components.

(1) GPC-FTIR Measurement Conditions

GPC apparatus: Prominence HPLC system (DGU-20A3/LC-20AD/SIL-20AHT/CTO-20A/SPD-20A/RID-10A/CBM-20A) (manufactured by Shimadzu Corporation)

Detector: differential refractometer (RI detector)

FT-IR interface: LC Tranceform 600 (manufactured by Lab Connection)

FT-IR: Nicolet iS10 (manufactured by Thermo Scientific)

Columns (from upstream): Guard Column HXL-L+G4000HXL+G3000HXL+G2000HXL×2 (7.8 mm ID×30 cm, manufactured by Tosoh Corporation), Eluent: THF (HPLC grade manufactured by FUJIFILM Wako Pure Chemical Corporation)

Flow rate: 1.0 mL/min.

Sample concentration: 2.0 mg/mL

Injection volume: 500 μL

Column temperature: 40° C.

Measurement wavenumbers: 5000 to 650 cm$^{-1}$

Resolution: 4 cm$^{-1}$

Number of scans: 8 times/1 point (2) Sample Pretreatment

A weighed sample with the eluent added was allowed to stand overnight for dissolution. The sample was then gently shaken and filtered through a 0.45 μm PTFE cartridge filter. No undissolved materials were visually observed.

(3) Molecular Weight Calculation Method

A third-order approximation curve constructed using the following standard polystyrenes (PS) manufactured by Tosoh Corporation was used as a calibration curve. Therefore, the molecular weights shown are molecular weights in terms of standard PS.

TSKgel Standard Polystyrene A-500: Nominal Mol. Wt. $5.9 \times 10^2$, Mw/Mn 1.19 (0005203/manufactured by Tosoh Corporation)

TSKgel Standard Polystyrene A-2500: Nominal Mol. Wt. $2.63 \times 10^3$, Mw/Mn 1.05 (0005205/manufactured by Tosoh Corporation)

TSKgel Standard Polystyrene A-5000: Nominal Mol. Wt. $5.06 \times 10^3$, Mw/Mn 1.02 (0005206/manufactured by Tosoh Corporation)

TSKgel Standard Polystyrene F-1: Nominal Mol. Wt. $1.02 \times 10^4$, Mw/Mn 1.02 (0005207/manufactured by Tosoh Corporation)

TSKgel Standard Polystyrene F-2: Nominal Mol. Wt. $1.74 \times 10^4$, Mw/Mn 1.01 (0005208/manufactured by Tosoh Corporation)

TSKgel Standard Polystyrene F-4: Nominal Mol. Wt. $3.79 \times 10^4$, Mw/Mn 1.01 (0005209/manufactured by Tosoh Corporation)

<Results of GPC-FTIR Analysis>

Figure 14:
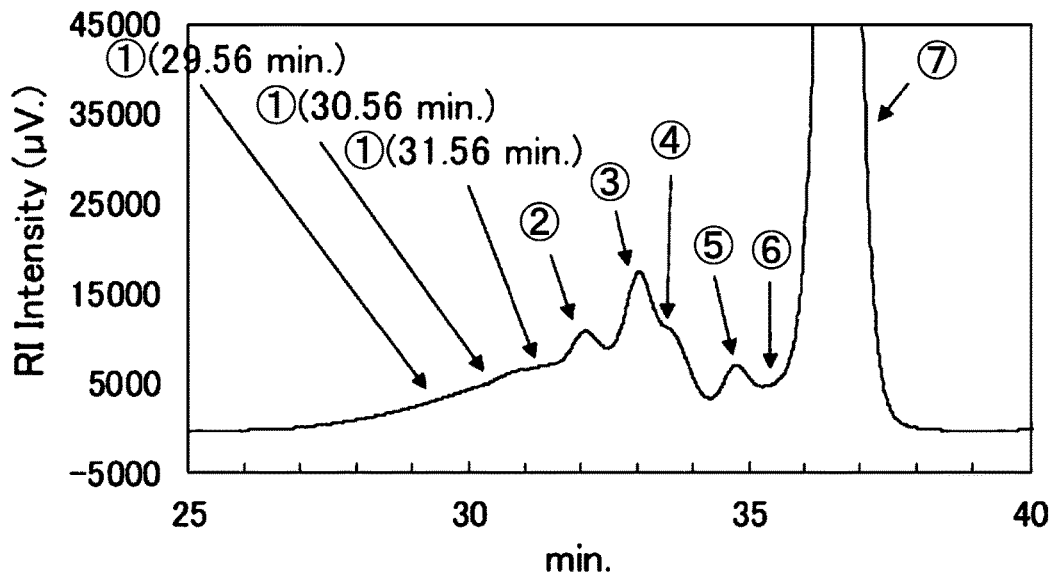
FIG. 14 shows a chromatogram and peak positions acquired by an RI detector in "Component analysis of compound (1a)-containing composition" in EXAMPLES.

The chromatogram and peak positions acquired by the RI detector are shown in FIG. 14.

Peak 7 in FIG. 14 is the peak of compound (1a).

Since the injection volume was increased in order to increase IR sensitivity, peak 4 and peak 6 were insufficiently separated.

Average molecular weights of the peaks are shown in Table 1 below. In Table 1, "Mn" represents number-average molecular weight, "Mw" represents weight-average molecular weight, "Mz" represents average molecular weight, and "Mw/Mn" represents polydispersity.

TABLE 1

|  | Mn | Mw | Mz | Mw/Mn |
|---|---|---|---|---|
| Peak 1 | 1300 | 1400 | 1600 | 1.1 |
| Peak 2 | 880 | 880 | 890 | 1.0 |
| Peak 3 | 730 | 730 | 730 | 1.0 |
| Peak 4 | 620 | 620 | 630 | 1.0 |
| Peak 5 | 500 | 500 | 500 | 1.0 |
| Peak 6 | 430 | 430 | 430 | 1.0 |
| Peak 7 | 320 | 320 | 320 | 1.0 |

As shown in Table 1, peak 1 in FIG. 14 was confirmed to be the peak of the compound group (A) having a molecular weight in the range of 1,000 to 10,000 in the present invention.

Figure 15:
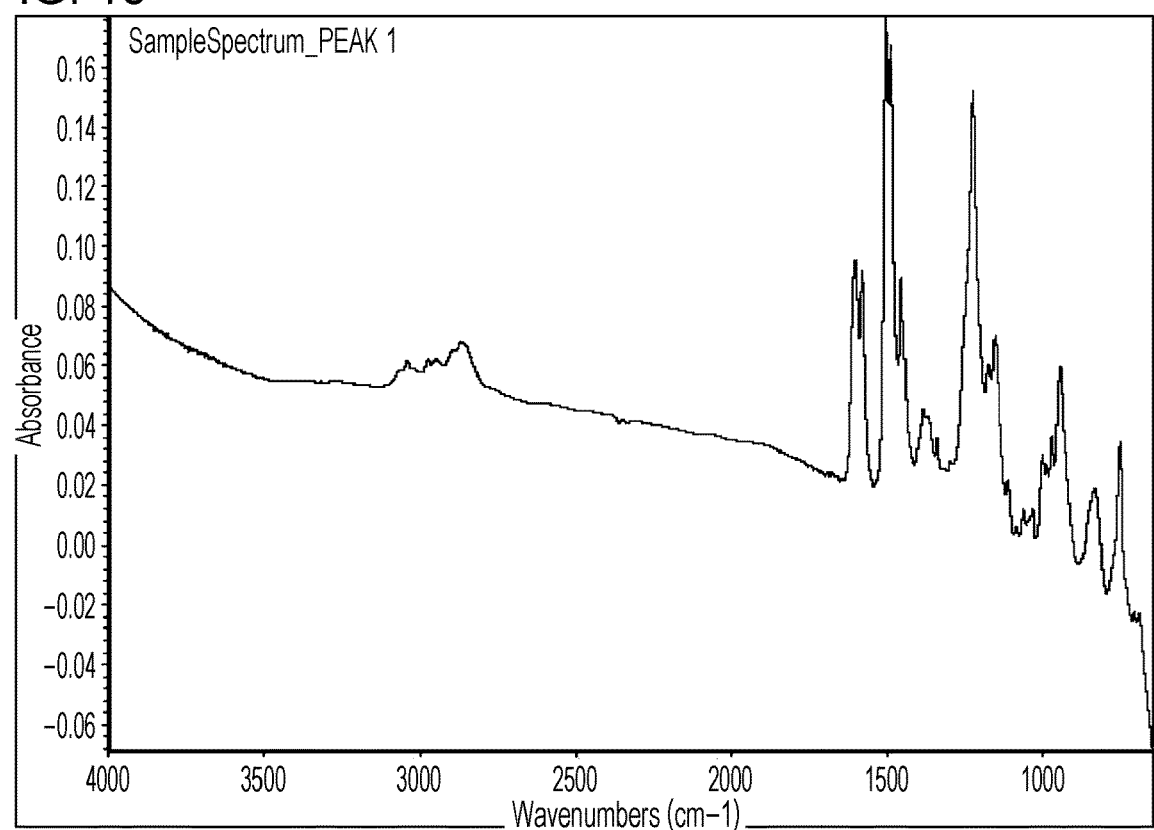
FIG. 15 shows an FT-IR spectrum of peak 1 (a peak of a compound group (A) having a molecular weight in the range of 1,000 to 10,000 in the present invention) in FIG. 14.
Figure 16:
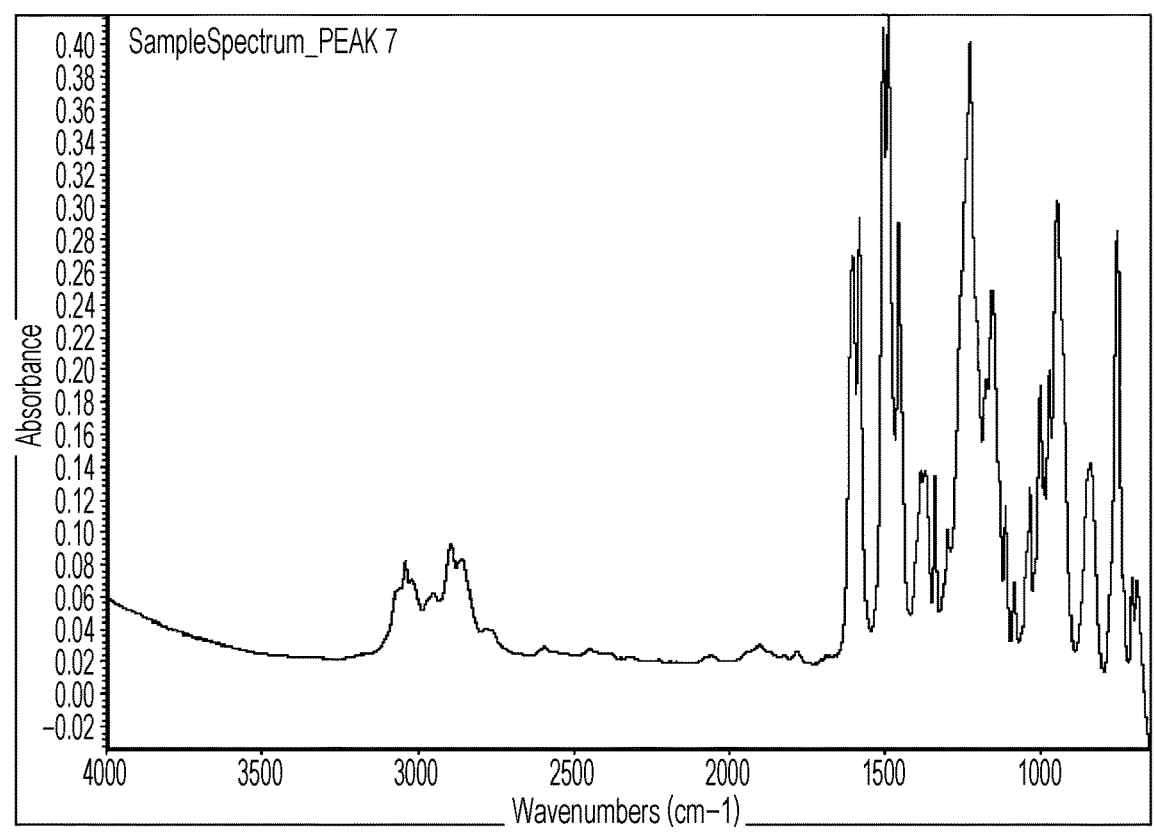
FIG. 16 shows an FT-IR spectrum of peak 7 (a peak indicating compound (1a)) in FIG. 14.

FT-IR spectra at peak tops of peak 1 (a peak indicating the compound group (A) having a molecular weight in the range of 1,000 to 10,000 in the present invention) and peak 7 (a peak indicating compound (1a)) in FIG. 14 are shown in FIGS. 15 and 16.

Figure 17:
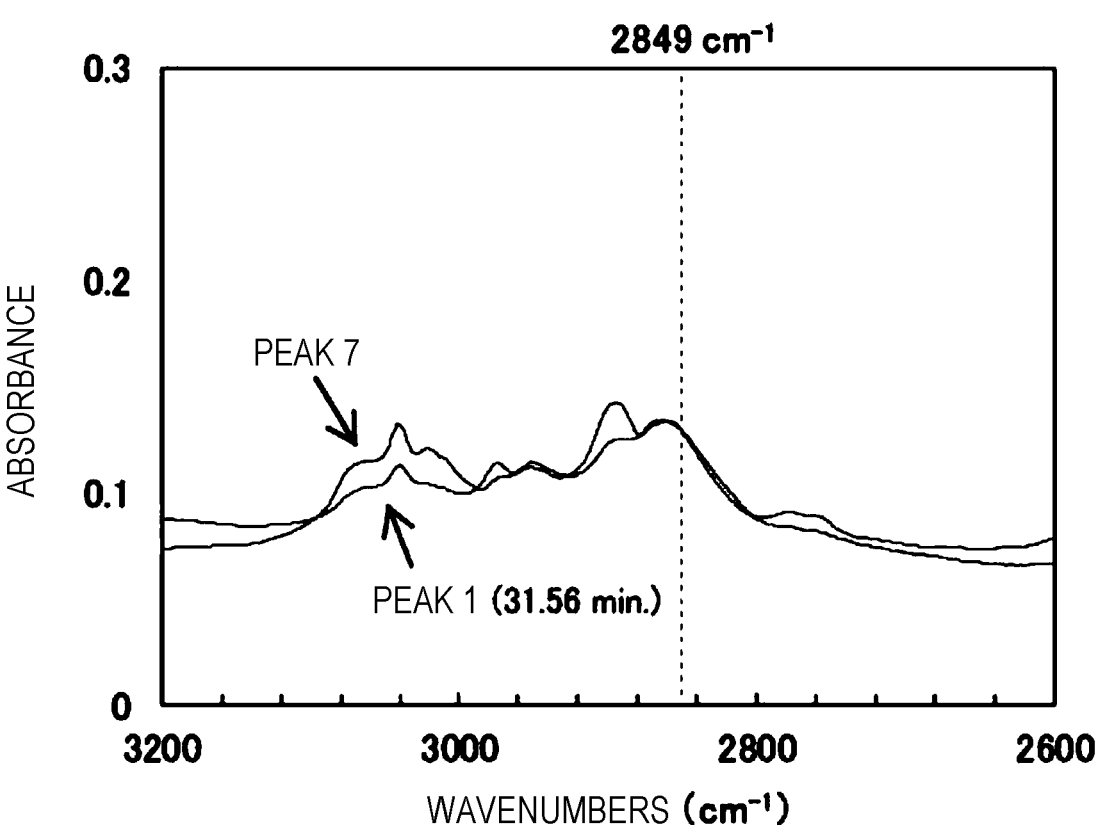
FIG. 17 shows an FT-IR spectrum in the range of 2600 to 3200 cm$^{-1}$ as normalized to the peak at 2849 cm$^{-1}$ on the basis of the FT-IR spectra of FIGS. 15 and 16.

FIG. 17 shows an FT-IR spectrum in the range of 2600 to 3200 $cm^{-1}$ as normalized to the peak at 2849 $cm^{-1}$, which indicates benzene ring C—H stretch, on the basis of the FT-IR spectra of FIGS. 15 and 16. It has been revealed that the compound group (A) having a molecular weight in the range of 1,000 to 10,000 in the present invention (peak 1) has a weaker peak intensity near 3000 $cm^{-1}$ than compound (1a) (peak 7).

The invention claimed is:

1. A benzoxazine compound-containing composition comprising a benzoxazine compound represented by general formula (1) below and a compound group (A) having a molecular weight in a range of 1,000 to 10,000, wherein the benzoxazine compound-containing composition is a reaction product obtained by adding 3,4'-diaminodiphenyl ether, over 1 to 10 hours, to a mixture of a formaldehyde selected from the group consisting of an aqueous formaldehyde solution, 1,3,5-trioxane, and paraformaldehyde; one or more phenol compounds selected from the group consisting of phenol, p-cresol, o-cresol, and m-cresol; and a solvent, wherein in a gel permeation chromatography measurement using a differential refractometer as a detector, a peak area of the compound group (A) is in a range of 0.1 area % to 15 area % relative to a peak area of all components detected, and the benzoxazine compound-containing composition has a melt viscosity at 100° C. in a range of 0.1 Pa·S to 4.5 Pa·S, (1)

wherein each R independently represents a hydrogen atom or a methyl group, wherein in the gel permeation chromatography measurement, a peak area of the benzoxazine compound represented by general formula (1) is in a range of 62 area % to 90 area % relative to the peak area of all components detected, provided that a sum total of the peak area of the benzoxazine compound represented by general formula (1), the peak area of the compound group (A), and a peak area of other components detected is 100 area %.

2. A curable resin composition comprising the benzoxazine containing composition according to claim 1.

3. The curable resin composition according to claim 2, comprising the benzoxazine compound-containing composition and at least one selected from the group consisting of epoxy resins, benzoxazine compounds other than the benzoxazine compound represented by general formula (1), and novolac phenol resins.

4. A cured product obtained by curing the curable resin composition according to claim 3.

5. A cured product obtained by curing the curable resin composition according to claim 2.

* * * * *